(12) United States Patent
Velaparthi et al.

(10) Patent No.: US 7,232,826 B2
(45) Date of Patent: Jun. 19, 2007

(54) TYROSINE KINASE INHIBITORS

(75) Inventors: Upender Velaparthi, North Haven, CT (US); Mark D. Wittman, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 324 days.

(21) Appl. No.: 10/674,098

(22) Filed: Sep. 29, 2003

(65) Prior Publication Data

US 2004/0092514 A1 May 13, 2004

Related U.S. Application Data

(60) Provisional application No. 60/415,066, filed on Sep. 30, 2002.

(51) Int. Cl.
*A61K 31/496* (2006.01)
*C07D 401/14* (2006.01)

(52) U.S. Cl. .................. 514/253.07; 544/363; 544/48; 544/49; 544/105; 544/235; 544/236; 544/237; 544/353

(58) Field of Classification Search ............... 544/363; 514/253.07
See application file for complete search history.

(56) References Cited

U.S. PATENT DOCUMENTS

| | | | | |
|---|---|---|---|---|
| 6,479,512 | B1 * | 11/2002 | Fraley et al. | 514/312 |
| 6,605,617 | B2 * | 8/2003 | Renhowe et al. | 514/312 |
| 2002/0103230 | A1 * | 8/2002 | Renhowe et al. | 514/338 |
| 2002/0107392 | A1 | 8/2002 | Renhowe et al. | |
| 2003/0028018 | A1 * | 2/2003 | Renhowe et al. | 544/60 |
| 2005/0256157 | A1 | 11/2005 | Gesner et al. | |
| 2005/0261307 | A1 | 11/2005 | Cai et al. | |

FOREIGN PATENT DOCUMENTS

| JP | 63-230687 | | 9/1988 |
|---|---|---|---|
| JP | 11321093 A | * | 11/1999 |
| WO | WO 02/22598 | | 3/2002 |
| WO | WO 2004/018419 | | 3/2004 |

OTHER PUBLICATIONS

Katzung et al. Basic and Clinical Pharmacology. Seventh Edition. Appleton& Lange. 1998. pp. 882-884.*
Emerging approaches to antiangiogenic therapies for treating cancer, posted Nov. 3, 2005 on http://www.nyas.org/ebriefreps/main.asp?intSubsectionID=3099.*
Burke Stem Cells, vol. 12, pp. 1-6 (1994).*
Brower Nature Biotech. vol. 17, pp. 963-968 (1999).*
Carmeliet et al. Nature, vol. 407, pp. 249-257 (2000).*
Hennequin et al. J.Med. Chem. vol. 42, pp. 5369-5389 (1999).*
Vippagunta et al. Advanced Drug Delivery Reviews, vol. 48, pp. 3-26 (2001).*
Pending U.S. Appl. No. 60/490,889, filed Jul. 29, 2003.
Pending U.S. Appl. No. 10/263,448, filed Oct. 2, 2002.
Pending U.S. Appl. No. 10/751,798, filed Jan. 5, 2004.

* cited by examiner

*Primary Examiner*—Emily Bernhardt
(74) *Attorney, Agent, or Firm*—Elliot Korsen; Maureen S. Gibbons

(57) ABSTRACT

The present invention provides compounds of Formula I or II that are useful as anti-cancer agents and other diseases that can be treated by inhibiting tyrosine kinase enzymes

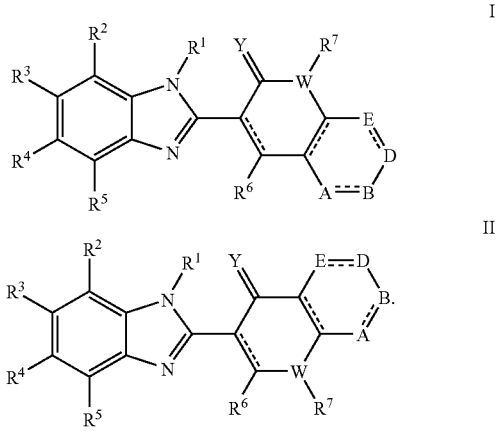

2 Claims, No Drawings

TYROSINE KINASE INHIBITORS

RELATED APPLICATIONS

This application claims priority benefit under Title 35 § 119(e) of U.S. provisional Application No. 60/415,066, filed Sep. 30, 2002, the contents of which are herein incorporated by reference.

FIELD OF INVENTION

The present invention relates generally to the field of tyrosine kinase enzyme inhibition using novel small molecules.

BACKGROUND OF THE INVENTION

Tyrosine Kinases are a class of enzymes, which catalyze the transfer of the terminal phosphate of adenosine triphosphate to the phenolic hydroxyl group of a tyrosine residue present in the target protein. Tyrosine kinases play a critical role in signal transduction for several cellular functions including cell proliferation, carcinogenesis, apoptosis, and cell differentiation (Plowman, G. D.; Ullrich, A.; Shawver, L. K.: Receptor Tyrosine Kinases As Targets For Drug Intervention. *DN&P* (1994) 7: 334-339). Therefore inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, HER-2, IGF-1R, IR, LCK, MEK, MET, PDGF, Src, and VEGF (Traxler, P. M. Protein Tyrosine Kinase Inhibitors in Cancer Treatment. *Exp. Opin. Ther. Patents* (1997) 7: 571-588; incorporated herein by reference). Hence, there is an ongoing need to investigate novel compounds that can be used to regulate or inhibit tyrosine kinase enzymes.

SUMMARY OF THE INVENTION

The present invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, angiogenic diseases and immunologic disorders (Powis, G.; Workman, P. Signaling targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

In addition to being used as single agents, it is contemplated that tyrosine kinase inhibitors can enhance the activity of cytotoxic or cytostatic treatments when used in combination with standard therapies known in the art.

The present invention is directed to compounds having Formula I or II

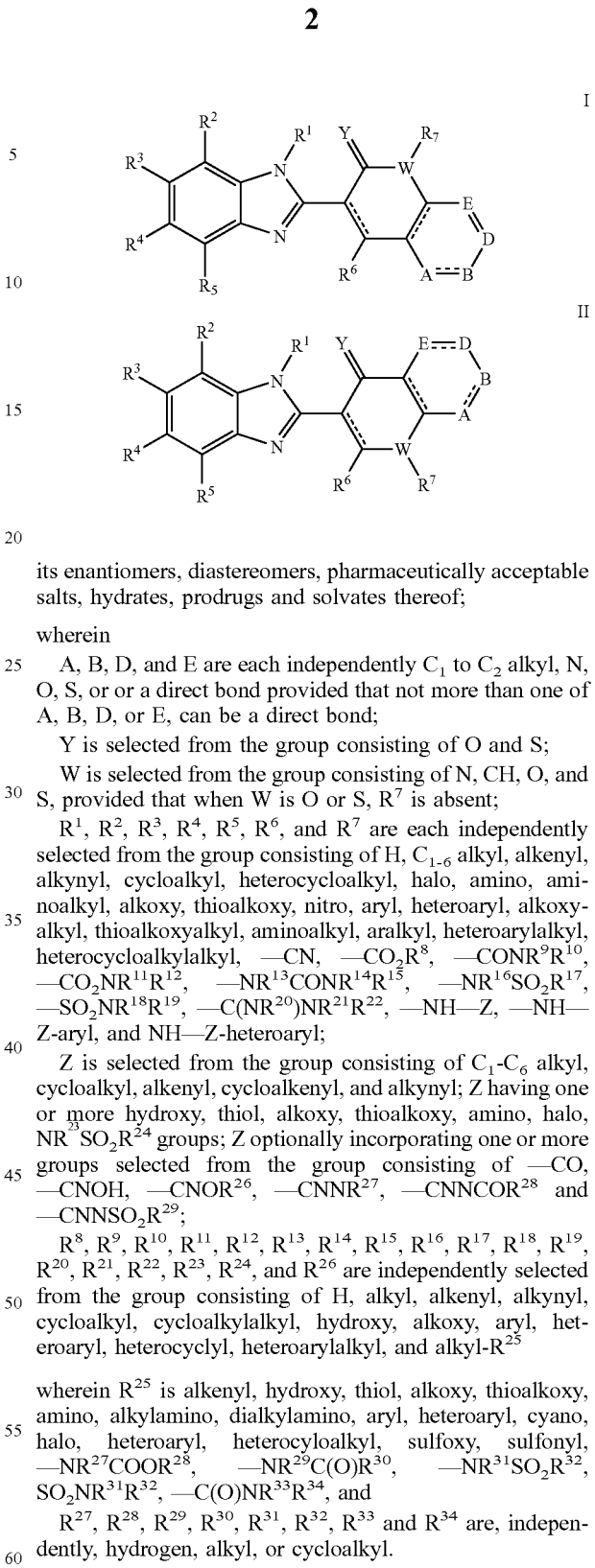

its enantiomers, diastereomers, pharmaceutically acceptable salts, hydrates, prodrugs and solvates thereof;

wherein

A, B, D, and E are each independently $C_1$ to $C_2$ alkyl, N, O, S, or or a direct bond provided that not more than one of A, B, D, or E, can be a direct bond;

Y is selected from the group consisting of O and S;

W is selected from the group consisting of N, CH, O, and S, provided that when W is O or S, $R^7$ is absent;

$R^1$, $R^2$, $R^3$, $R^4$, $R^5$, $R^6$, and $R^7$ are each independently selected from the group consisting of H, $C_{1-6}$ alkyl, alkenyl, alkynyl, cycloalkyl, heterocycloalkyl, halo, amino, aminoalkyl, alkoxy, thioalkoxy, nitro, aryl, heteroaryl, alkoxyalkyl, thioalkoxyalkyl, aminoalkyl, aralkyl, heteroarylalkyl, heterocycloalkylalkyl, —CN, —$CO_2R^8$, —$CONR^9R^{10}$, —$CO_2NR^{11}R^{12}$, —$NR^{13}CONR^{14}R^{15}$, —$NR^{16}SO_2R^{17}$, —$SO_2NR^{18}R^{19}$, —$C(NR^{20})NR^{21}R^{22}$, —NH—Z, —NH—Z-aryl, and NH—Z-heteroaryl;

Z is selected from the group consisting of $C_1$-$C_6$ alkyl, cycloalkyl, alkenyl, cycloalkenyl, and alkynyl; Z having one or more hydroxy, thiol, alkoxy, thioalkoxy, amino, halo, $NR^{23}SO_2R^{24}$ groups; Z optionally incorporating one or more groups selected from the group consisting of —CO, —CNOH, —$CNOR^{26}$, —$CNNR^{27}$, —$CNNCOR^{28}$ and —$CNNSO_2R^{29}$;

$R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —$NR^{27}COOR^{28}$, —$NR^{29}C(O)R^{30}$, —$NR^{31}SO_2R^{32}$, $SO_2NR^{31}R^{32}$, —$C(O)NR^{33}R^{34}$, and $R^{27}$, $R^{28}$, $R^{29}$, $R^{30}$, $R^{31}$, $R^{32}$, $R^{33}$ and $R^{34}$ are, independently, hydrogen, alkyl, or cycloalkyl.

DESCRIPTION

The present invention provides for compounds of Formula I or II, as defined above, pharmaceutical compositions employing such compounds and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, at any available point of attachment. When the alkyl group is said to be substituted with an alkyl group, this is used interchangeably with "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: hydroxy, halo (such as F, Cl, Br, I), haloalkyl (such as $CCl_3$ or $CF_3$), alkoxy, alkylthio, cyano, carboxy (—COOH), alkylcarbonyl (—C(O)R), alkoxycarbonyl (—OCOR), amino, carbamoyl (—NHCOOR or —OCONHR), urea (—NHCONHR), thiol, (—SH), sulfoxy, sulfonyl, aryl, heteroaryl, and heterocycloalkyl. Alkyl groups as defined may also comprise one or more carbon to carbon double bonds or one or more carbon to carbon triple bonds. Alkyl groups may also be represented by the formula alkyl-$R^{25}$. In preferred embodiments, the alkyl group is a methyl, ethyl, propyl or butyl group and includes substituted methyl, ethyl, propyl or butyl groups.

The term "alkenyl" herein alone or as part of another group refers to a hydrocarbon radical straight, branched or cyclic containing from 2 to 12 carbon atoms and at least one carbon to carbon double bond. An alkenyl group may be optionally substituted in the same manner as described for an alkyl group.

The term "alkynyl" herein alone or as part of another group refers to a hydrocarbon radical straight, branched or cyclic containing from 2 to 12 carbon atoms and at least one carbon to carbon triple bond. An alkynyl group may be optionally substituted in the same manner as described for an alkyl group.

The term "alkoxy" as used alone or in combination herein refers to a straight or branched chain alkyl group covalently bonded to the parent molecule through an oxygen atom linkage containing from one to ten carbon atoms and the terms "$C_{1-6}$ alkoxy" and "lower alkoxy" refer to such groups containing from one to six carbon atoms. Examples include, but are not limited to, methoxy, ethoxy, propoxy, isopropoxy, butoxy, t-butoxy and the like. The term "optionally substituted" when used in connection with an alkoxy substituent refers to the replacement of up to two hydrogens, preferably on different carbon atoms with a radical selected from the group of lower alkyl, phenyl, cyano, halo, trifluoromethyl, nitro, hydroxy, alkanoyl, amino, monoalkyl amino and dialkylamino. Alkoxy groups may be substituted in the same manner that alkyl groups can be substituted as described above.

The term "sulfoxy" herein alone or as part of a group refers to —SO and may be substituted with, for example, alkyl, aryl or heteroaryl groups.

The term "sulfonyl" herein alone or as part of a group refers to —$SO_2$ and may be substituted with alkyl, aryl or heteroaryl groups.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. Preferred substituents include alkylamino and dialkylamino, such as methylamino, ethylamino, dimethylamino, and diethylamino. These substituents may be further substituted with a carboxylic acid or any of the alkyl or aryl substituents set out herein. In addition, the amino substituents may be taken together with the nitrogen atom to which they are attached to form 1-pyrrolidinyl, 1-piperidinyl, 1-azepinyl, 4-morpholinyl, 4-thiamorpholinyl, 4-sulfoxymorpholine, 4-sulfonylmorpholine, 1-piperazinyl, 4-alkyl-1-piperazinyl, 4-arylalkyl-1-piperazinyl, 4-diarylalkyl-1-piperazinyl, 1-homopiperazinyl, 4-alkyl-1-homopiperazinyl, 4-arylalkyl-1-homopiperazinyl, 4-diarylalkyl-1-homopiperazinyl; 1-pyrrolidinyl, 1-piperidinyl, or 1-azepinyl, optionally substituted with alkyl, alkoxy, alkylthio, halo, trifluoromethyl or hydroxy.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, alkynyl, alkoxy, hydroxy, carboxy, carbamoyl, alkyloxycarbonyl, alkylaminocarbonyl, nitro, trifluoromethyl, amino, cycloalkyl, cyano, alkyl $S(O)_m$ (m=0, 1, 2), or thiol. Aryl groups may also be substituted with heterocycloalkyl and heterocycloaryl groups to form fused rings, such as dihydrobenzfuranyl, oxindolyl, indolyl, indolinyl, oxindolyl, benzoxazolidinonyl, benzoxazolinyl and benzoxazolidinone.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, preferably one, selected from the group consisting of halo, alkyl, substituted alkyl, alkenyl, alkynyl, nitro, cyano, oxo (=O), hydroxy, alkoxy, thioalkyl, —$CO_2H$, —OC(=O)H, $CO_2$-alkyl, —OC(=O)alkyl, =N—OH, =N—O-alkyl, aryl, heteroaryl, heterocyclo, a five or six membered ketal (i.e. 1,3-dioxolane or 1,3-dioxane), —NR'R", —C(=O)NR'R", —OC(=O)NR'R", —NR'CO$_2$R", —NR'C(=O)R", —SO$_2$NR'R", and —NR'SO$_2$R", wherein each of R' and R" is independently selected from hydrogen, alkyl, substituted alkyl, and cycloalkyl, or R' and R" together form a heterocyclo or heteroaryl ring. Cycloalkyl groups may also be substituted with hetero atoms such as O, N, and S to form heterocycloalkyl groups. Preferred heterocycloalkyl groups include optionally substituted morpholine, homomorpholine (7 membered ring), thiomorpholine, piperazine, homopiperazine (7 membered ring), and piperidine.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, hydroxy, alkoxy, thioalkyl, —CO$_2$H, —OC(=O)H, —CO$_2$-alkyl, —OC(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —OC(=O)NR'R", —NR'CO$_2$'R", —NR'C(=O)R", —SO$_2$NR'R", and —NR'SO$_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrrolidinyl, imidazolinyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, and the like.

Exemplary bicyclic heteroaryl groups include indolyl, indolinyl, oxindolyl, benzoxazolidinone, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

The term "halogen" or "halo" herein alone or as part of another group refers to chlorine, bromine, fluorine or iodine selected on an independent basis.

The term "hydroxy" herein alone or as part of another group refers to —OH.

The term "thioalkoxy" herein alone or as part of another group refers to an alkyl group as defined herein attached to the parent molecular group through a sulfur atom. Examples of thioalkoxy include, but are not limited to, thiomethoxy, thioethoxy, and the like.

Abbreviations: "Ph" represents phenyl; "Me" represents methyl; and "Et" represents ethyl.

An "anti-cancer agent" as used herein includes known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as irinotecan or topotecan; tubulin interacting agents, such as paclitaxel, docetaxel or the epothilones; hormonal agents, such as tamoxifen; thymidilate synthase inhibitors, such as 5-fluorouracil; antimetabolites, such as methotrexate; tyrosine kinase inhibitors such as Iressa and Tarceva; angiogenesis inhibitors; EGF inhibitors; VEGF inhibitors; CDK inhibitors; Her1/2 inhibitors and monoclonal antibodies directed against growth factor receptors such as erbitux (EGF), herceptin (Her2), or avastin (VEGF).

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

When $C_{1-6}$ alkyl, alkenyl, alkynyl, cycloalkyl are substituted, they are preferably substituted with one or more hydroxy, cyano, carbamoyl, hydroxy, alkoxy, thiol, alkenyl, thioalkoxy, amino, alkylamino, amido, sulfonyl, sulfoxy, sulfonamido, halo, heterocycloalkyl, aryl or heteroaryl.

When aryl or heteroaryl are substituted, they are preferably substituted with one or more alkyl, alkenyl, alkynyl, cyano, carbamoyl, hydroxy, alkoxy, thioalkoxy, amino, amido, sulfonamido, halo or with R', R" wherein R', R" form a ring that is fused to the aryl group. When CH$_2$aryl or heteroaryl are substituted, they are preferably substituted with one or more alkyl, alkenyl, alkynyl, cyano, carbamoyl, hydroxy, alkoxy, thioalkoxy, amino, amido, sulfonamido, or halogen.

When NH—Z-aryl or NH—Z-heteroaryl groups are substituted, they are preferably substituted with one or more alkyl, alkenyl, alkynyl, hydroxy, alkoxy, thioalkoxy, amino, halogen, nitro, nitrile, carboxylate, alkoxycarbonyl, carbamoyl, ester, amide, aryl, or heteroaryl groups.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "alkyl-R$^{25}$" includes optionally substituted alkyl groups such as methyl, ethyl, propyl, and butyl, attached to an R$^{25}$ group. R$^{25}$ generally includes hydrogen, alkenyl, hydroxy, thiol, alkoxy, thioalkoxy, amino, alkylamino, dialkylamino, aryl, heteroaryl, cyano, halo, sulfoxy, sulfonyl, —NHCOOH, —NHC(O)—, —NHSO$_2$—, —C(O)NH$_2$, heteroaryl or heterocycloalkyl groups such as morpholinyl or a group having the formula:

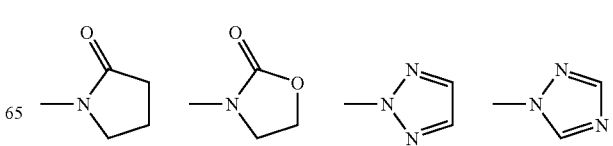

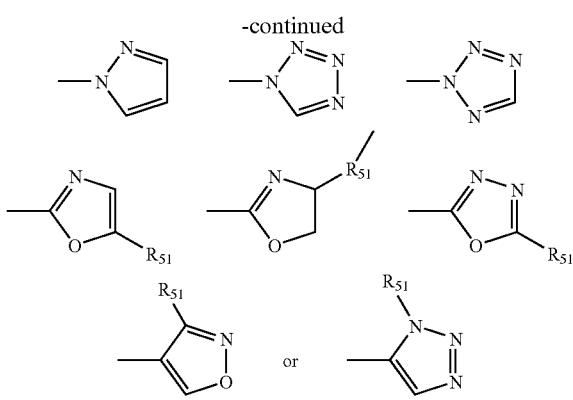

wherein $R_{51}$ is H or alkyl.

The terms "imidazole" and "imidazoline" herein alone or as part of another group includes substituted imidazoles and substituted imidazolines. Similarly, the term "tetrahydropyrimidine" includes substituted tetrahydropyrimidines. Likewise, the terms "piperazine", "piperidine" "morpholines", "homopiperazines", "homomorpholines" and "pyrrolidine" include substituted piperazines, substituted piperidines, substituted morpholines, substituted homomorpholines and substituted pyrrolidines, respectively.

Compounds of the present invention have the general Formula I or II:

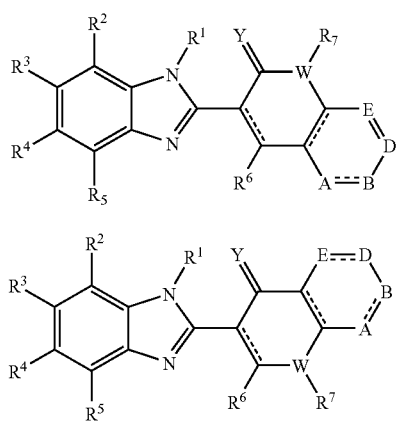

including all enantiomers, diastereomers, pharmaceutically acceptable salts, hydrates, prodrugs and solvates thereof wherein A, B, D, and E are independently $C_1$ to $C_2$ alkyl, N, O, S or a direct bond, provided that not more than one of A, B, D, or E is a direct bond;

Y is selected from the group consisting of O and S;

W is selected from the group consisting of NH, $CH_2$, O, and S, provided that when W is O or S, $R^7$ is absent;

$R^1$, $R^2$, $R^3$, $R^4$, $R^5$, $R^6$, and $R^7$ are each independently selected from the group consisting of H, $C_{1-6}$alkyl, alkenyl, alkynyl, cycloalkyl, heterocycloalkyl, halo, amino, aminoalkyl, alkoxy, thioalkoxy, nitro, aryl, heteroaryl, alkoxyalkyl, thioalkoxyalkyl, aminoalkyl, aralkyl, heteroarylalkyl, heterocycloalkylalkyl, —CN, —$CO_2R^8$, —$CONR^9R^{10}$, —$CO_2NR^{11}R^{12}$, —$NR^{13}CONR^{14}R^{15}$, —$NR^{16}SO_2R^{17}$, —$SO_2NR^{18}R^{19}$, —$C(NR^{20})NR^{21}R_{22}$, —NH—Z, —NH—Z-aryl, and NH—Z-heteroaryl;

Z is selected from the group consisting of $C_1$-$C_6$alkyl, cycloalkyl, alkenyl, cycloalkenyl, and alkynyl; Z having one or more hydroxy, thiol, alkoxy, thioalkoxy, amino, halo, $NR^{23}SO_2R^{24}$ groups; Z optionally incorporating one or more groups selected from the group consisting of —CO, —CNOH, —$CNOR^{26}$, —$CNNR^{27}$, —$CNNCOR^{28}$ and —$CNNSO_2R^{29}$; and $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{23}$, $R^{24}$, and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —$NR^{27}COOR^{28}$, —$NR^{29}C(O)R^{30}$, —$NR^{31}SO_2R^{32}$, $SO^2NR^{31}R^{32}$ —$C(O)NR^{33}R^{34}$, and $R^{27}$, $R^{28}$, $R^{29}$, $R^{30}$, $R^{31}$, $R^{32}$, $R^{33}$ and $R^{34}$ are, independently, hydrogen, alkyl, or cycloalkyl.

In one preferred embodiment, A, B, D, and E are each C, Y is O, and W is N.

In some preferred embodiments, $R^6$ is H, nitro, —NH—Z, —NH—Z-aryl, —NH—Z-heteroaryl, —$NR^{31}SO_2R^{32}$, or $SO^2NR^{31}R^{32}$ and $R^3$ is an optionally substituted piperazine or an optionally subsituted homopiperazine.

According to one embodiment, $R^1$ and $R^7$ are H; Y is O; W is N; and $R^3$ is selected from the group consisting of alkoxy, imidazole, imidazoline, tetrahydropyrimidine, piperazine, morpholine, homomorpholine, piperidine, pyrrolidine, homopiperazine and amino, preferably piperazine; $R^5$ is selected from the group consisting of H, methyl, ethyl, isopropyl, secondary butyl, cyclopropyl, F, $CF_3$, $OCH_3$, and amino; and $R^6$ is selected from the group consisting of H, —NH—Z, —NH—Z-aryl, and —NH—Z-heteroaryl. Preferred $R^6$ groups include —$NHCH_2CH(OH)$aryl or $NHCH(CH_2OH)CH_2$aryl. Preferred aryl groups include optionally substituted phenyls wherein the substituents are halogens or alkoxy groups.

According to some embodiments of the present invention, $R^3$ is morpholine, thiomorpholine, sulfoxymorpholine, sulfonylmorpholine, homomorpholine, or a substituted morpholine, thiomorpholine, sulfoxymorpholine, sulfonylmorpholine, or homomorpholine. Preferred substituents include hydroxy, thiol, amino, alkylamino, dialkylamino, alkoxy, or thioalkoxy. In other embodiments, $R^3$ is $(CH_2)_n$-morpholine or $(CH_2)_n$— piperazine, wherein n is 0 to 3.

Suitable examples of salts of the compounds according to the invention include inorganic or organic acids. These include, but are not limited to, hydrochloride, hydrobromide, sulfate, methanesulfonate, maleate, fumarate, phosphate and other pharmaceutically acceptable salts. Salts which are unsuitable for pharmaceutical uses but which can be employed, for example, for the isolation or purification of free compounds of Formula I or II or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography.

The individual optical isomers can be obtained from the racemates by conventional methods, such as, for example, salt formation with an optically active acid followed by crystallization.

It should be understood that the present invention includes prodrug forms of the compounds of Formula I or II. Various forms of prodrugs are well known in the art. For examples of such prodrug derivatives, see:
(a) Design of Prodrugs, edited by H. Bundgaard (Elsevier, 1985); and Methods in Enzymology, Vol. 42, pp. 309-396, edited by K. Widder et al., (Academic Press, 1985);
(b) A Textbook of Drug Design and Development, edited by Krosgaard-Larsen and H. Bundgaard, Chapter 5, "Design and Application of Prodrugs," by H. Bundgaard, pp. 113-191 (1991);
(c) H. Bundgaard, Advanced Drug Deliver Reviews, 8, pp. 1-38 (1992);
(d) H. Bundgaard et al., Journal of Pharmaceutical Sciences, 77, 285 (1988); and
(e) N. Kayeka et al., Chem. Phar. Bull., 32, 692 (1984).

The invention also provides a pharmaceutical composition comprising a compound of Formula I or II, as defined above, and a pharmaceutically acceptable carrier and at least one other anti-cancer agent formulated as a fixed dose. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound.

In order to maintain such a constant concentration, a continuous intravenous delivery device may be utilized. An example of such a device is the Deltec CADD-PLUS.™. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

Preferred anti-cancer agents are selected from the group consisting of: tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone; a tyrosine kinase inhibitor such as Iressa or Tarceva; an angiogenesis inhibitor; an EGF inhibitor; a VEGF inhibitor; a CDK inhibitor; a Her1/2 inhibitor and monoclonal antibodies directed against growth factor receptors such as erbitux (EGF) and herceptin (Her2).

The invention further provides a method of treating a condition via modulation of at least one tyrosine kinase enzyme comprising administering to a mammalian species in need of such treatment an effective amount of a compound of Formula I or II, as defined above.

Additionally, the invention provides a method of treating a condition via modulation of at least one tyrosine kinase enzyme comprising administering to a mammalian species in need of such treatment an effective amount of a compound of Formula I or II, as defined above, in combination (simultaneously or sequentially) with at least one other anti-cancer agent.

A preferred condition, treated by said methods of the instant invention, is cancer. Additionally, the tyrosine kinase enzyme may include (but is not limited to): Abl, CDK's, EGF, EMT, FGF, FAK, Flk-1/KDR, HER-2, IGF-1R, IR, LCK, MEK, MET, PDGF, Src, and VEGF.

The invention also provides a method for treating cancer, comprising administering to a mammalian species in need of such treatment, a therapeutically effective amount of at least one of the pharmaceutical compositions defined above.

The invention further provides a method for treating proliferative diseases, comprising administering to a mammalian species in need of such treatment a therapeutically effective amount of at least one of the pharmaceutical compositions defined above.

Certain compounds of Formula I or II may generally be prepared according to the following schemes and the knowledge of one skilled in the art. Solvates (e.g., hydrates) of the compounds of Formula I or II are also within the scope of the present invention. Methods of solvation are generally known in the art. Accordingly, the compounds of the instant invention may be in the free or hydrate form, and may be obtained by methods exemplified by the following schemes below.

The present invention also encompasses a pharmaceutical composition useful in the treatment of cancer, comprising a therapeutically effective compounds having formula I or II, with or without pharmaceutically acceptable carriers or diluents. The pharmaceutical compositions of this invention comprise an optional anti-proliferative agent, a compound formula I or II, and a pharmaceutically acceptable carrier. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, compounds of formula I or II, and compositions of the present invention may be administered orally or parenterally including the intravenous, intramuscular, intraperitoneal, subcutaneous, rectal and topical routes of administration.

For oral use, the compounds and compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added. In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration. Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The compounds of the present invention may also be delivered transdermally. The transdermal compositions can take the form of creams, lotions, aerosols and/or emulsions and can be included in a transdermal patch of the matrix or reservoir type as are conventional in the art for this purpose. The combinations of the present invention may also be used in conjunction with other well known therapies that are selected for their particular usefulness against the condition that is being treated Schemes I-VII illustrate the preparation of compounds claimed in this invention. The examples, which follow, illustrate the compounds that can be synthesized by these schemes. The schemes are not limited by the examples listed or by any substituents employed for illustrative purposes.

Scheme I describes the preparation of the benzimidazoles. The starting diamines 1 are readily available using literature methods or are obtained commercially. The diamine is then condensed with an aldehyde 2 to provide the benzimidazole 3. Further modification of the functional groups on the aryl group of the benzimidazole or heterocycle of 3 is then possible.

Scheme I

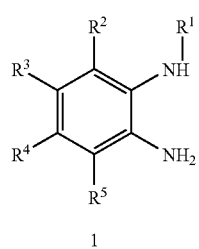

1

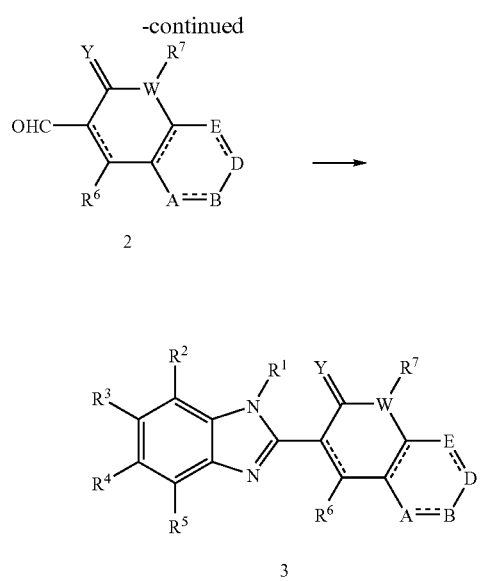

Alternatively, the benzimidazole could be formed in a step-wise manner (see Scheme II) by amide formation using the acid chloride of 5 or any of the commonly used peptide coupling reagents such as DCC (dicyclohexylcarbodiimide), EDCI (1-(3-dimethylaminopropyl)-3-ethylcarbodiimide hydrochloride), etc. Once the amide 6 is formed the nitro group is reduced using catalytic hydrogenation, transfer hydrogenation or chemical reduction with $SnCl_2$ or iron powder or other methods known in the art for reduction of aryl nitro groups. Treatment of the aniline with acid forms the benzimidazole.

Scheme II

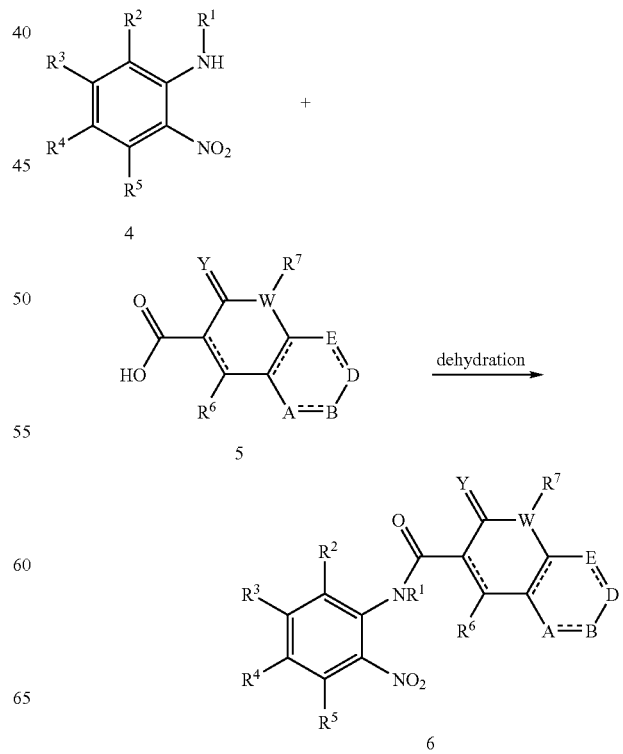

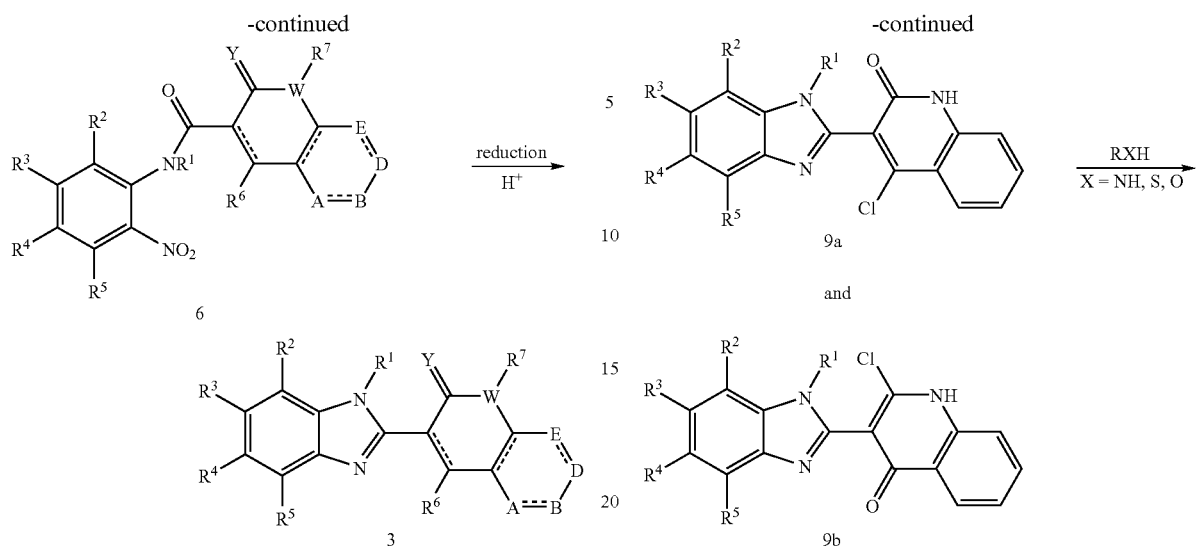

For example, Scheme III illustrates the use of 2,4-dichloro-3-quinoline carboxaldehyde 7 to provide the functionalized benzimidazole 8. Hydrolysis of the chloro group using protic acid provided a mixture of quinolones 9a and 9b which can be separated by standard chromatographic techniques well known in the art of synthetic chemistry. Addition of heteroatom nucleophiles such as amines, alcohols or thiols to 9a,b provides the substituted napthopyridones 10a, b. Other functionality can be incorporated into the aldehyde. The above example is included for illustrative purposes only.

Scheme III

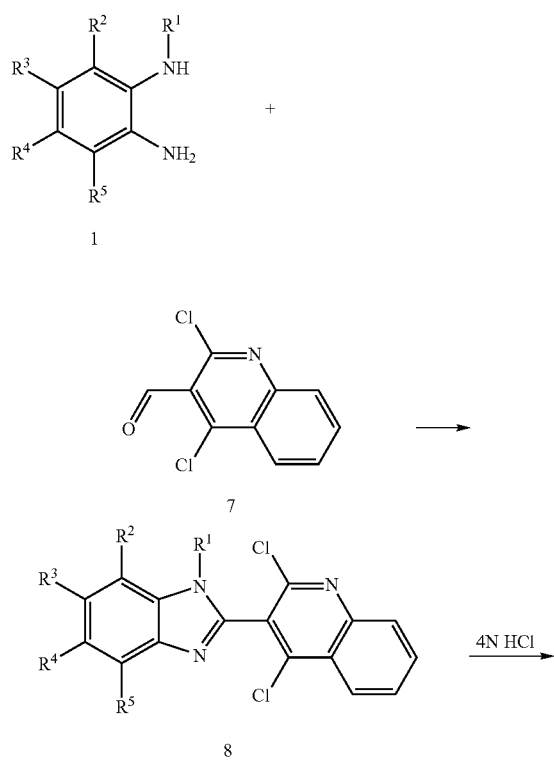

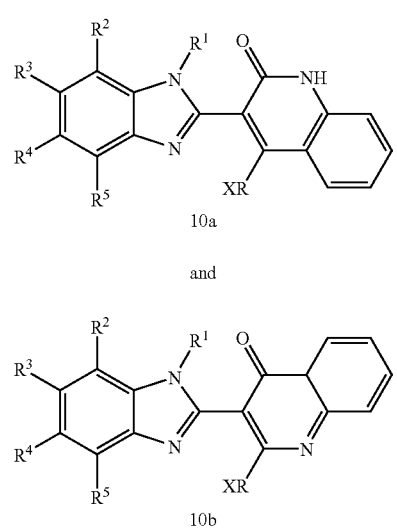

Likewise the aryl ring of the benzimidazole prepared using Schemes I or II can be modified. For example introduction of a cyano group for $R^3$ on the benzimidazole allows for the formation of heterocycles such as imidazolines, oxazolines, thiazolines, amides, or amidines. Scheme IV illustrates such transformations. Starting from the cyano-substituted benzimidazole 11 the heterocycle can be modified as illustrated in Scheme IV to provide 12. Imidate formation preferably using ethanol and acid provides intermediate 13. Imidate 13 can be transformed using diamines to form imidazolines, amino alcohols to form oxazolines, amino acetals to form imidazoles, and amino thiols to form thiazolines 14. Alternatively the imidate can be hydrolyzed to the acid and coupled with amines using any of the standard amide formation reagents (DCC, EDCI, etc.) to form amides 15. Imidate 13 is also a useful intermediate for the preparation of amidines 16 by reacting with amines.

Scheme IV

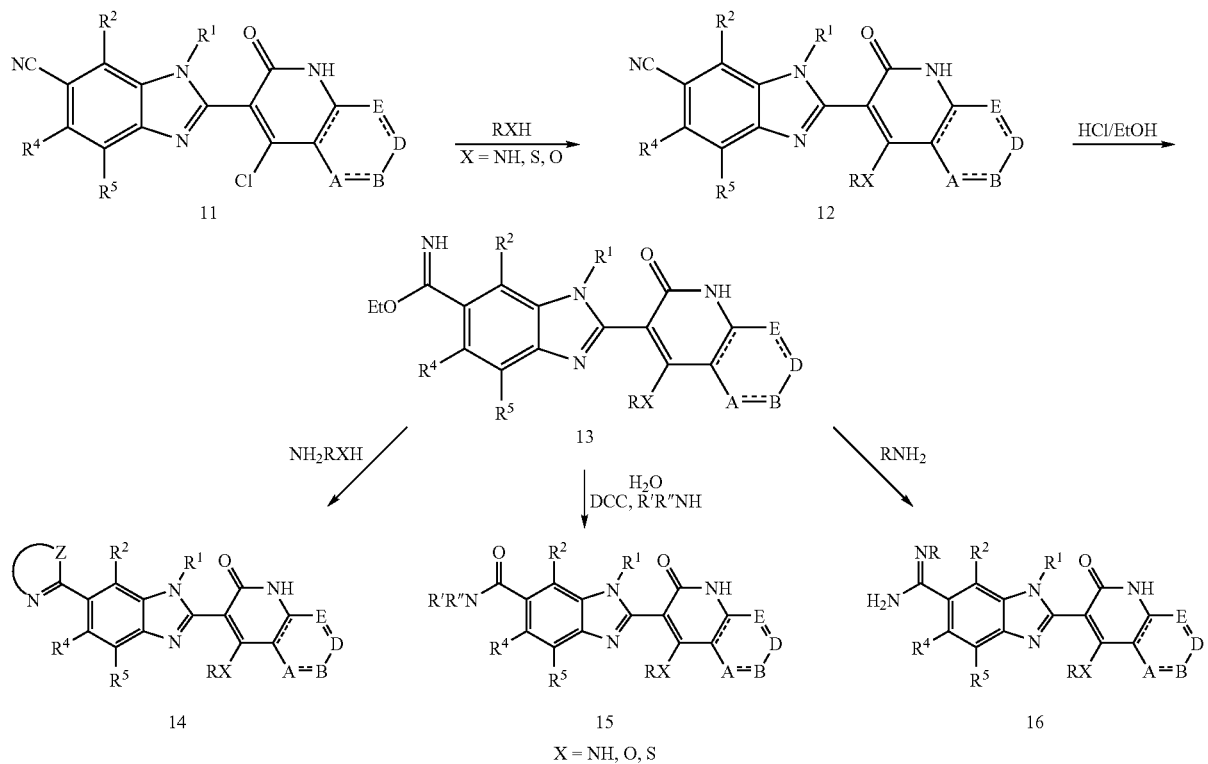

The cyano group of 12 can also be reduced to the aldehyde 17 as in Scheme V using diisobutylaluminum hydride to provide a substrate for reductive amination. Reaction of the aldehyde with an amine and NaCNBH$_3$ would provide the amine 18. Many variants of this reductive amination reaction are known and are envisioned in which the reducing agent or imine forming reagent are varied such as sodium triacetoxyborohydride, sodium borohydride or pyridine-borane complex in combination with agents to promote imine formation such as sulfuric acid, MgSO$_4$, azetropic removal of water using benzene or toluene, molecular sieves, or titanium isopropoxide. Using this reaction scheme any amine especially heterocyclic amines could be used such as morpholine, piperazine, homopiperazine, piperadine, pyrolidine, etc.

Scheme V

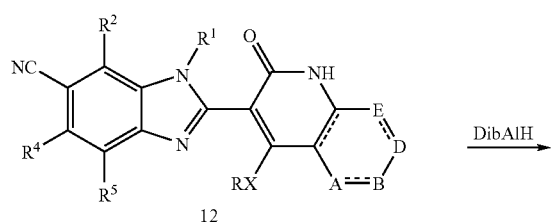

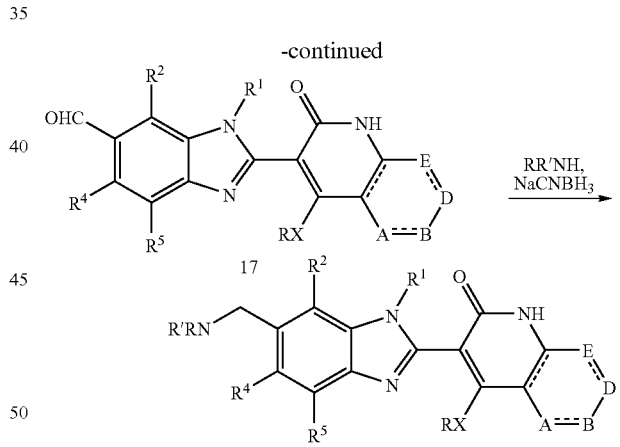

Scheme VI illustrates further transformation of benzimidazoles that bear a halogen atom using palladium catalysis according to conditions developed by Suzuki [Yang et al. Acta Chem. Scand. (1993) 221; Suzuki et al. Synth. Commun. (1981) 11: 513] or Buckwald/Hartwig [Buchwald et al. J. Am. Chem. Soc. (1994) 116: 7901; Hartwig et al. J. Am. Chem. Soc. (1994) 116: 5969; Hartwig. Angew. Chem., Int. Ed. Engl. (1998) 37: 2046] and variations of these methods. These disclosures are all incorporated by reference herein. Preparation of a bromide substituted benzimidazole 19 provides a substrate for Suzuki coupling with aryl, vinyl, and heterocyclic boronic acids to provide benzimidazoles 20. Likewise, amines and heterocycles such as piperazine or morpholine derivatives 21 can be prepared from the same bromide using amines under conditions described by Buchwald and Hartwig or variations thereof.

Scheme VI

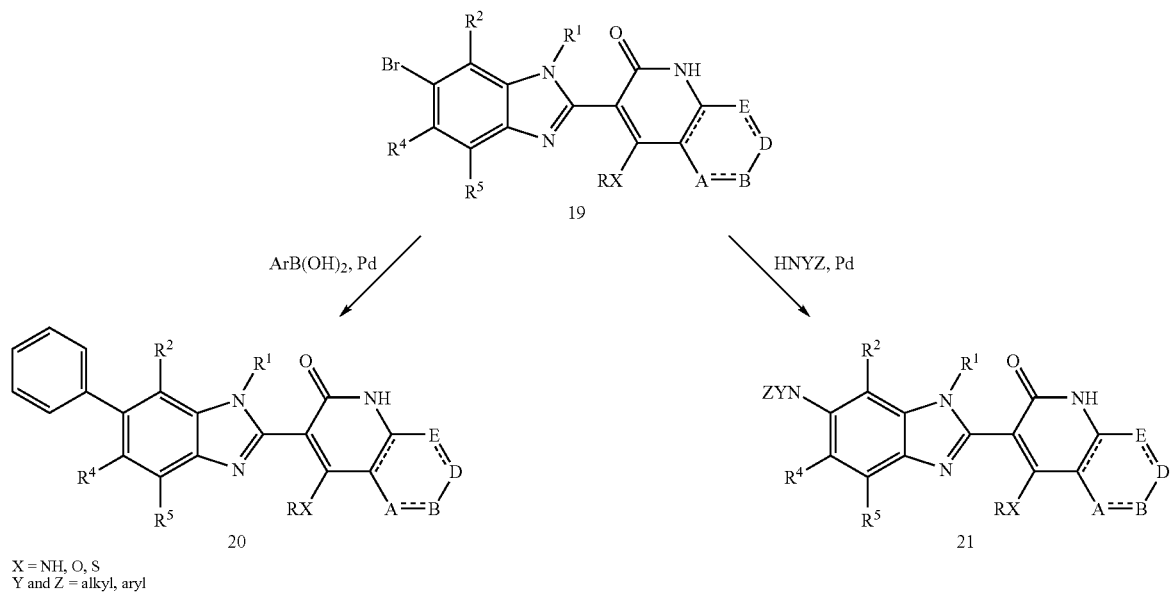

X = NH, O, S
Y and Z = alkyl, aryl

Alternatively amine and heterocyclic derivatives such as 21 can be prepared using intermediate 6 described in Scheme II and VII. When the $R^3$ of 6 is a halogen, preferably F, the halogen can be displaced with amines, heterocyclic amines and other nitrogen containing heterocycles such as piperazine, piperidine, morpholine, imidazole, etc (Scheme VII). Following the example illustrated in Scheme VII compounds such as 21 are prepared.

Scheme VII

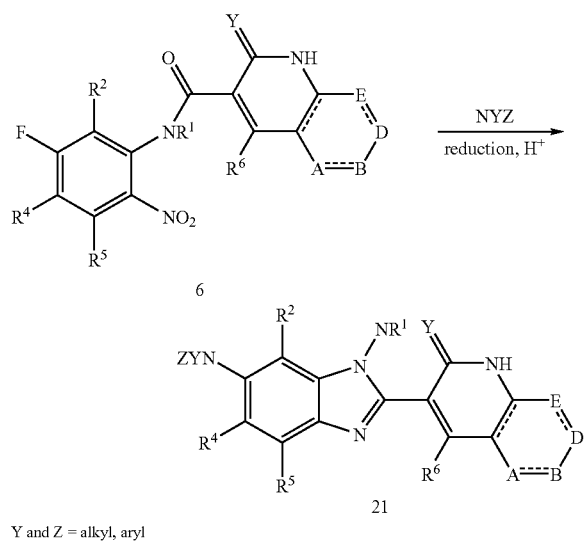

Y and Z = alkyl, aryl

Utility

The compounds according to the invention are tyrosine kinase enzyme inhibitors and thus are useful in the therapy of a variety of proliferative diseases (including but not limited to diseases associated with tyrosine kinase enzymes) such as cancer, autoimmune diseases, viral diseases, fungal diseases, neurodegenerative disorders and cardiovascular disease.

More specifically, the compounds of Formula I or II are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including sarcoma, melanoma, seminoma, teratocarcinoma, osteosarcoma, xenoderoma pigmentosum, keratoctanthoma, thyroid follicular cancer and Kaposi's sarcoma.

Due to the key role of tyrosine kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula I or II may induce apoptosis. The apoptotic response is aberrant in a variety of human diseases. Compounds of Formula I or II, as modulators of apoptosis, will be useful in the treatment of cancer (including but not limited to those types mentioned herein above), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula I or II may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula I or II may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula I or II may also be useful in inhibiting tumor angiogenesis and metastasis.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as irinotecan or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methotrexate; tyrosine kinase inhibitors such as Iressa and Tarceva; angiogenesis inhibitors; EGF inhibitors; VEGF inhibitors; CDK inhibitors; Her1/2 inhibitors and monoclonal antibodies directed against growth factor receptors such as Erbitux™, also known as C225 (EGF), Herceptin™, also known as trastuzamab, (Her2), or Avastin™ (VEGF).

If formulated as a fixed dose, such combination products employ the compounds of this invention within the dosage range described below and the other pharmaceutically active agent or treatment within its approved dosage range. Compounds of Formula I or II may also be administered sequentially with known anticancer or cytotoxic agents when a combination formulation is inappropriate. The invention is not limited in the sequence of administration; compounds of Formula I or II may be administered either prior to or after administration of the known anticancer or cytotoxic agent(s).

Further subject matter of the invention also includes pharmaceuticals for use, as described above, including controlling cancer, inflammation and arthritis, which contain at least one compound of the Formula I or II as defined above or at least one of its pharmacologically acceptable acid addition salts, and the use of a compound of the Formula I or II as defined above for the preparation of a pharmaceutical having activity against proliferative diseases as described previously including against cancer, inflammation and/or arthritis.

The pharmacological properties of the compounds of this invention may be confirmed by a number of pharmacological assays. The exemplified pharmacological assays which follow have been carried out with the compounds according to the invention and their salts.

Biological Assays

A. CDK 2/Cyclin E Kinase Assay

Kinase reactions consisted of 5 ng of baculovirus expressed GST-CDK2/cyclin E complex, 0.5 µg GST-RB fusion protein (amino acids 776-928 of retinoblastoma protein), 0.2 µCi $^{33}$P γ-ATP, 25 µM ATP in 50 µl kinase buffer (50 mM Hepes, pH 8.0, 10 mM MgCl$_2$, 1 mM EGTA, 2 mM DTT). Reactions were incubated for 45 minutes at 30° C. and stopped by the addition of cold trichloroacetic acid (TCA) to a final concentration of 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required inhibiting 50% of kinase activity (IC$_{50}$). Compounds were dissolved at 10 mM in dimethylsulfoxide (DMSO) and evaluated at six concentrations, each in triplicate. The final concentration of DMSO in the assay equaled 2%. IC$_{50}$ values were derived by non-linear regression analysis and have a coefficient of variance (SD/mean, n=6)=14%.

B. EMT Kinase Assay

A filter-based kinase assay, measuring the phosphorylation of Gst-SLP76 by Gst-Emtk, was employed to determine the compound inhibitory activity against Emt. The kinase reaction was performed in a 96-well plate at room temperature for 15 min before being terminated by adding 100 µl of 20% trichloroacetic acid (TCA) containing 0.1 M sodium pyrophosphate. The kinase reaction mixture (60 µl) contained 25 mM HEPES, pH 7.0, 0.1 mg/ml BSA, 5 mM MgCl$_2$, 5 mM MnCl$_2$, 8 ng of enzyme (Gst-Emtk), 5 µg of the substrate protein (Gst-SLP76), 1 µM ATP, 0.4 µCi of [γ-P$^{33}$]ATP and the tested compound (at various concentrations). After termination, the proteins were allowed to precipitate in the presence of TCA for 1 hr at 4° C. The precipitated proteins were then harvested on a filter plate (UniFilter-96, GF/C, Packard Instrument) and washed to remove excess [γ-P$^{33}$]ATP. The radioactivity was determined using a TopCount NXT (Packard Instrument) after adding 35 µl of Microscint 20 (Packard Instrument).

C. FAK Tyrosine Kinase Assay

The Focal Adhesion kinase was assayed using the synthetic polymer poly(Glu/Tyr) (Sigma Chemicals) as a phosphoacceptor substrate. Each reaction mixture consisted of a total volume of 50 ul and contained 100 ng of baculovirus-expressed enzyme, 2 µg of poly(Glu/Tyr), 1 µM of ATP, and 0.2 µCi of [γ-$^{33}$P]ATP. The mixtures also contained 40 mM Tris.HCl, pH 7.4, 1 mM MnCl$_2$, 0.5 mM DTT, and 0.1 mg/ml bovine serum albumin. The reaction mixtures were incubated at 26° C. for 1 hour and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived non-linear regression analysis and have a coefficient of variance (SD/mean, n=6)=16%.

D. HER-1/HER-2 Kinase Assay

Kinase reactions consisted of 10 ng of baculovirus expressed GST- HER1, 100 ng of HER2, 100 ng/ml poly(Glu/Tyr) (Sigma), 0.2 µCi 33P γ-ATP, 1 µM ATP in 50 µl kinase buffer (50 mM Tris, pH 7.5, 10 mM MnCl2, 0.5 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at six concentrations, each in triplicate. The final concentration of DMSO in the assay equaled 1%. $IC_{50}$ values were derived by non-linear regression analysis and have a coefficient of variance (SD/mean, n=6)=16%.

E. IGF—Receptor Tyrosine Kinase Assay

The IGF-1 receptor tyrosine kinase was assayed using the synthetic polymer poly(Glu/Tyr) (Sigma Chemicals) as a phosphoacceptor substrate. Each reaction mixture consisted of a total volume of 50 ul and contained 125 ng of baculovirus expressed enzyme, 2.5 µg of poly(Glu/Tyr), 25 µM of ATP, and 0.1 µCi of [γ-$^{33}$P]ATP. The mixtures also contained 20 mM MOPS, pH 7.0, 5 mM $MnCl_2$, 0.5 mM DDT, and 0.1 mg/ml bovine serum albumin. The reaction mixtures were incubated at 30° C. for 45 minutes and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived by non-linear regression analysis and have a coefficient of variance (SD/mean, n=6)= 16%.

F. Insulin Receptor Tyrosine Kinase Assay

The Insulin Receptor Tryrosine kinase was assayed using the synthetic polymer poly(Glu/Tyr) (Sigma Chemicals) as a phosphoacceptor substrate. Each reaction mixture consisted of a total volume of 50 ul and contained 90 ng of baculovirus-expressed enzyme, 2.5 µg of poly(Glu/Tyr), 25 µM of ATP, and 0.1 µCi of [γ-$^{33}$P]ATP. The mixtures contained also 20 mM Tris.HCl, pH 7.4, 5 mM $MnCl_2$, 0.5 mM DTT, and 0.1 mg/ml bovine serum. The reaction mixtures were incubated at 26° C. for 1 hour and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived non-linear regression analysis and have a coefficient of variance (SD/mean, n=6) =16%.

G. LCK Kinase Assay

Kinase reactions consisted of 10 ng of baculovirus expressed 10 ng GST-Lck, 100 ng/ml poly(Glu/Tyr) (Sigma), 0.2 µCi 33P γ-ATP, 1 µM ATP in 50 µl kinase buffer (50 mM Tris, pH 7.5, 10 mM MnCl2, 0.5 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at six concentrations, each in triplicate. The final concentration of DMSO in the assay equaled 1%. $IC_{50}$ values were derived by non-linear regression analysis and have a coefficient of variance (SD/mean, n=6)=16%.

H. MET Kinase Assay

Kinase reactions consisted of 10 ng of baculovirus expressed GST-Met, 2.5 ug poly(Glu/Tyr) (Sigma), 0.2 µCi 33P γ-ATP, 10 µM ATP in 50 µl kinase buffer (40 mM Tris, pH 7.5, 1 mM MnCl2, 0.50 mM DTT). Reactions were incubated for 1 h at 27 C and stopped by the addition of cold trichloroacetic acid (TCA) to a final concentration 3.5%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate. The final concentration of DMSO in the assay equaled 1%. $IC_{50}$ values were derived by non-linear regression analysis and have a coefficient of variance (SD/mean, n=6)=16%.

I. PDGF Receptor Kinase Assay

Kinase reactions consisted of 70 ng of baculovirus expressed GST-PDGFbR, 0.3 ug biotinylated poly(Glu/Tyr) (Sigma), in 50 µl kinase buffer (20 mM Hepes, pH 7.5, 0.7 uM ATP, 10 mM MnCl2, 0.5 mM DTT, 0.15 mM NaCl, 0.1 mg/ml BSA). Reactions were incubated for 30 minutes at room temperature with shaking and stopped by the addition of 10 ul of 0.2M EDTA, pH8.0. 150 ul of HTRF detection buffer was added and incubated for 1 hour and 30 minutes at room temperature. Counts were quantitated on Discovery HTRF Packard Instrument.

J. VEGFR-2 (KDR) Kinase Assay

Kinase reactions consisted of 7.5 ng of baculovirus expressed GST-KDR, 1.5 ug poly(Glu/Tyr) (Sigma), 0.04 µCi 33P γ-ATP, 2.5 µM ATP in 50 µl kinase buffer (25 mM Tris, pH 7.5, 1.8 mM MnCl2, 0.0.625 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at six concentrations, each in triplicate. The final concentration of DMSO in the assay equaled 1%. $IC_{50}$ values were derived by non-linear regression analysis and have a coefficient of variance (SD/mean, n=6)=16%.

K. Cytotoxicity Assay (HT-29-Colon; Colo205, MCF-7-Breast)

Tumor cell lines are maintained in McCoy's 5A medium (GIBCO) and 10% heat inactivated fetal bovine serum (GIBCO). The in vitro cytotoxicity is assessed in tumor cells by a tetrazolium-based colorimetric assay which takes advantage of the metabolic conversion of MTS (3-(4,5-dimethylthiazol-2-yl)-5-(3-carboxymethoxyphenyl)-2-(4-sulphenyl)-2H-tetrazolium, inner salt) (Promega) to a reduced form that absorbs light at 492 nm (1). Cells are seeded 24 hr prior to drug addition. Following a 72 hour incubation at 37° C. with serially diluted test compound, MTS (Riss, T. L, et al., Comparison of MTT, XTT, and a novel tetrazolium compound MTS for in vitro proliferation and chemosensitivity assays.,"*Mol. Biol. Cell* 3 (Suppl.): 184a, 1992), in combination with the electron coupling agent phenazine methosulfate, is added to the cells. The incubation is continued for 3 hours, then the absorbency of the medium at 492 nm is measured with a spectrophotometer to obtain the number of surviving cells relative to control populations. The results are expressed as median cytotoxic concentrations ($IC_{50}$ values).

Biological Activity (uM); compounds of the present invention exhibit kinase activity of <25 uM against one or more of the following kinases CDK, EMT, FAK, Her1, Her2, IGF, IR, LCK, MET, PDGF, VEGF. HT-29 and Colo205 are human colon tumor cell lines and MCF-7 is a human breast tumor cell line.

General Procedure for the Preparation of 2-Hydroxy-2-(substituted-phenyl)-ethylamines 1-(3-Chloro-phenyl)-2-nitro-ethanol

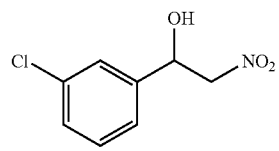

To a solution of 3-chloro-benzaldehyde (20 g, 0.142 mol) in nitromethane (100 mL) were added magnesium sulfate (37.6 g, 0.312 mol) and phosphazene base $P_1$-t-bu-tris (tetramethylene) (4.43 g, 0.014 mol). The reaction mixture was stirred at room temperature for 2 h. After concentration in vacuo, the residue was purified by flash chromatography (25% EtOAc/hexane) to yield the title compound (26.4 g, 100%) as a green-yellow oil. $^1$H NMR (300 MHz, DMSO-$d_6$) δ 7.53 (1H, s), 7.35-7.42 (3H, m), 6.23 (1H, broad s), 5.32-5.33 (1H, m), 4.90 (1H, dd, J=3.2, 12.4 Hz), 4.60 (1H), dd, J=1.2, 12.4 Hz).

[1-(3-Chloro-phenyl)-2-nitro-ethoxy]-triethyl-silane

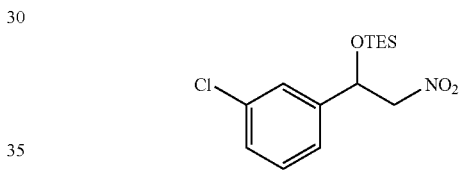

To a solution of 1-(3-chloro-phenyl)-2-nitro-ethanol (26 g, 0.14 mol) in DMF (50 mL) were added imidazole (28.6 g, 0.42 mol) and chlorotriethylsilane (25.3 g, 0.17 mol). The reaction mixture was stirred at room temperature for 2 h. After quenching with water, the mixture was extracted with ethyl acetate. The combined organic layers were washed with water and brine, dried over $Na_2SO_4$, and filtered. After removal of solvent, the crude product was purified by flash chromatography (2% EtOAc/hexane) to yield the title compound (37 g, 91%) as a colorless oil. $^1$H NMR (300 MHz, CDCl$_3$) δ 7.40 (1H, s), 7.27-7.32 (3H, m), 5.40 (1H, dd, J=3.2, 9.5 Hz), 4.51 (1H, dd, J=9.5, 12.1 Hz), 4.36 (1H, dd, J=3.3, 12.1 Hz), 0.85 (9H, t, J=7.5 Hz), 0.54 (6H, q, J=7.5 Hz).

2-(3-Chloro-phenyl)-2-triethylsilanyloxy-ethylamine

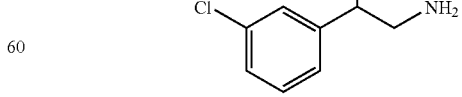

Raney nickel (1 g) was washed with distilled water five times and methanol three times. [1-(3-Chloro-phenyl)-2-nitro-ethoxy]-triethyl-silane (10 g, 0.032 mol) and Raney nickel in methanol (100 mL) was hydrogenated (35 psi) at room temperature for 14 h. The reaction mixture was filtered through a pad of celite and rinsed with methanol. Concentration of the filtrate to dryness gave the title compound (5.6 g, 62%) as a colorless oil which was used for the next step without purification. $^1$H NMR (300 MHz, CDCl$_3$) δ 7.32 (1H, s), 7.18-7.26 (3H, m), 4.70 (1H, t, J=5.8 Hz), 2.86 (2H, m), 0.89 (9H, t, J=7.9 Hz), 0.56 (6H, q, J=7.8 Hz). LRMS (M+H)$^+$ m/z 286.

General Procedure for the Preparation of 2-Hydroxy-2-(substituted-phenyl)-ethylamines

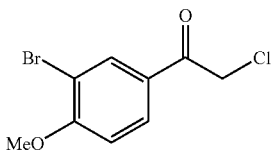

4-methoxy-3-bromophenyl chloroacetophenone: To a suspension of AlCl$_3$ (13.4 g, 0.10 mol) in methylene chloride (40 mL) was added a solution of 2-bromoanisole (12.5 mL, 0.10 mol) and chloroacetyl chloride (8 mL, 0.10 mol) at 0° C. The solution was warmed to ambient temperature for two hours and poured onto ice and extracted with methylene chloride, washed with saturated sodium bicarbonate solution, brine, and dried over MgSO$_4$. The solution was filtered, concentrated and crystallized from EtOH to give 15.37 g of white solid. LRMS [M−H]−260.8; IR (KBr) 1697, 1048, 1255 cm$^{-1}$; $^1$H NMR (300 MHz, CDCl$_3$) δ 8.18 (s, 1H), 7.94 (dd, J=8.67 Hz, 1H), 6.96 (d, J=8.67 Hz, 1H), 4.62 (s, 2H), 3.98 (s, 3H); $^{13}$C NMR (CDCl$_3$, 75.5 Hz) δ 188.8, 160.3, 134.1, 129.9, 128.2, 112.4, 111.3, 56.6, 45.3.

(S)-1-[4-methoxy-3-bromophenyl]-2-chloro ethanol

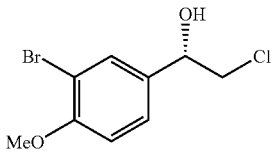

To a solution of (S)-Methyl-CBS-oxazaborolidine (1M in toluene, 0.745 mL, 0.745 mmol) and BH$_3$-THF (8 mL, 8 mmol) was added at the same time a solution of BH$_3$-THF (19 mL, 19 mmol) and a solution of the chloroketone (10.03 g, 37.98 mmol) in 19 mL of THF. Both solutions were added dropwise over 30 minutes. The solution was stirred for 1 hour and quenched with the slow addition of methanol (50 mL). The solution was concentrated and the residue chromatographed over a short silica gel column (1:1 hexane/ethyl acetate) to give a quantitative yield (10.0 g) of chlorohydrin as a clear oil. IR (KBr) 1053, 1258, 3406 cm$^{-1}$; $^1$H NMR (300 MHz, CDCl$_3$) δ 7.59 (s, 1H), 7.30 (dd, J=2.16 Hz, 1H), 6.90 (d, J=8.46 Hz, 1H), 4.83 (dd, J=3.57 Hz, 1H), 3.90 (s, 3H), 3.64 (ddd, J=3.6, 11.1, 8.7, 2H), 2.04 (b s, 1H). $^{13}$C NMR (CDCl$_3$, 75.5 MHz) δ 155.9, 133.5, 131.1, 126.3, 111.9, 73.1, 60.4, 56.3, 50.7.

(S) 2-Amino-1-[3-chloro-4-methoxyphenyl]ethanol Hydrochloride

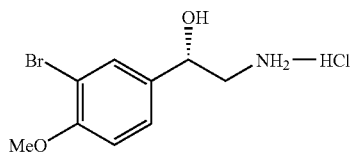

To a solution of the chlorohydrin (10.0 g, 37.9 mmol) in 120 mL of methanol at −40° C. was added 100 grams of ammonia. The solution was sealed in a pressure bottle and warmed to ambient temperature and stirred for 48 hours. The solution was cooled and opened. The ammonia was allowed to evaporate and solution concentrated. The residue was crystalized from ethanol/ethyl acetate to give 3.83 g of white solid (35%). The material was reacted with Boc$_2$O in ethyl acetate and saturated sodium bicarbonate and analyzed by chiral HPLC using a chiralcel OJ column using 95% hexane/ethanol as elutant and determined to by 98% ee. Additional crops were collected −2.96 g and 1.41 g for a total of 75% yield. LRMS [M+H]+246; IR (cm$^{-1}$, KBr) 1055, 1261, 3001, 2948, 3356; $^1$H NMR (500 MHz, DMSO) δ 8.09 (b s, 2 H), 7.58 (s, 1H), 7.36 (dd, J=2.05, 6.45 Hz, 1H), 7.11 (d, J=8.5 Hz, 1H) 6.10 (s, 1H), 4.80 (m, 1H), 3.84 (s, 3H), 3.00 (ddd, J=2.7, 12.6, 9.5 Hz, 2H); $^{13}$C NMR (DMSO, 75.5 MHz) δ 154.8, 135.4, 130.4, 126.6, 112.4, 110.4, 67.9, 56.2, 45.4.

(S) 2-Amino-1-[3-chlorophenyl]ethanol Hydrochloride

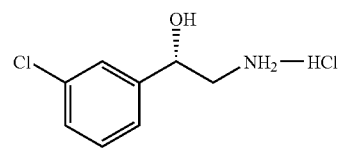

: was prepared according to the general procedure outlined above. LRMS [M+H]+172; IR (KBr, cm-1) 3048, 3351, 2952; $^1$H NMR (300 MHz, MeOD) δ 7.48 (s, 1H), 7.35 (m, 3H), 3.31 (ddd, J=1.5, 3.12, 9.15 Hz 2H).

(S)-2-Amino-1-[3-bromophenyl]ethanol Hydrochloride

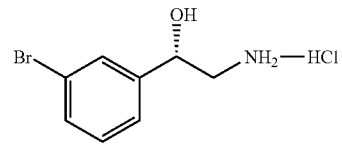

was prepared according to the general procedure outlined above. LRMS [MH]+217.9; IR (KBr, cm-1) 3025, 3443, 2891; $^1$H NMR (500 MHz, DMSO) δ 7.93 (b s, 2H), 7.60 (s, 1H), 7.52 (d, 1H), 7.41 (s, 1H), 7.35 (d, J=7.7 Hz, 1H) 6.17 (s, 1H), 4.82 (m, 1H), 3.08 (ddd, J=2.6, 12.7, 9.6 Hz, 2H); $^{13}$C NMR (DMSO, 75.5 MHz) δ 144.4, 130.5, 128.7, 125.0, 121.6, 68.3, 45.1.

(S)-2-Amino-1-[3-chloro-4-methylthiophenyl]ethanol Hydrochloride

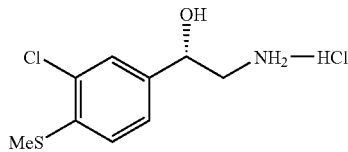

was prepared according to the general procedure outlined above. LRMS [M+H]+217.9; IR (KBr, cm-1) 3007, 3358; $^1$H NMR (500 MHz, DMSO) δ 8.12 (b s, 2H), 7.46 (s, 1H), 7.37 (s, 1H), 7.35 (d, 1H) 6.19 (d, 1H), 4.83 (m, 1H), 3.01 (ddd, J=3.2, 12.8, 9.3 Hz, 2H); $^{13}$C NMR (DMSO, 75.5 MHz) δ 139.6, 136.5, 129.8, 126.6, 125.4, 68.0, 45.2, 14.2.

(S)-2-Amino-1-[3-chloro-4-fluoro-phenyl]ethanol Hydrochloride

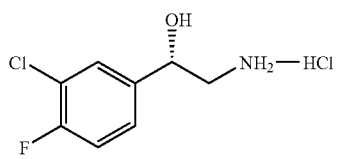

was prepared according to the general procedure outlined above. LRMS [M+H]+189.9; IR (KBr, cm-1) 1509, 3008, 3359; $^1$H NMR (500 MHz, DMSO) δ 8.21 (b s, 2H), 7.61 (d, J=7.85 Hz, 1H), 7.42 (m, 2H), 6.29 (s, 1H), 4.88 (m, 1H), 3.03 (ddd, J=3.4, 12.8, 9.2 Hz, 2H); $^{13}$C NMR (DMSO, 75.5 MHz) δ 157.5, 155.5, 139.7, 128.1, 126.7, 119.3, 116.7, 109.0, 67.8, 45.2.

(S)-2-Amino-1-[3-chloro-4-methoxyphenyl]ethanol Hydrochloride

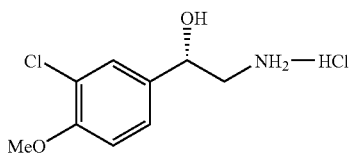

was prepared according to the general procedure outlined above. LRMS [M+H]+202; IR (KBr, cm-1) 3354, 3003, 2949, 1288, 1064; $^1$H NMR (500 MHz, DMSO) δ 8.18 (brs, 3H), 7.43 (d, J=2.0 Hz, 1H), 7.31 (dd, J=8.5, 2.0 Hz, 1H), 7.14 (d, J=5.1 Hz, 1H), 6.11 (s, 1H), 4.81 (m, 1H), 3.84 (s, 3H), 2.99 (dd, J=13, 3.5 Hz, 1H), 2.83 (dd, J=12.5, 9 Hz, 1H); $^{13}$C NMR (DMSO, 125 MHz) δ 153.9, 135.0, 127.3, 125.8, 120.8, 112.6, 68.0, 56.1, 45.5; Elemental Analysis Calcd for $C_9H_{12}ClNO_2$—HCl: C, 45.39; H, 5.50; N, 5.88. Found: C, 45.38; H, 5.43; N, 5.70.

(S)-2-Amino-1-(7-bromo-2,3-dihydrobenzfuran-5-yl)-2-aminoethanol Hydrochloride

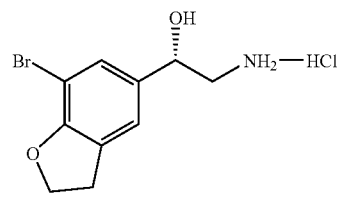

was prepared according to the general procedure outlined above. LRMS [M+H]+258; IR (KBr, cm-1) 3349, 3006, 2928, 1485, 1045, 983; $^1$H NMR (500 MHz, DMSO) δ 8.13 (brs, 3H), 7.29 (s, 1H), 7.23 (s, 1H), 6.08 (d, J=4 Hz, 1H), 4.76 (m, 1H), 4.61 (t, J=9 Hz, 2H), 3.29 (t, J=9 Hz, 2H), 2.96 (dd, J=13, 3.5 Hz, 1H), 2.82 (dd, J=13,9.5 Hz, 1H); $^{13}$C NMR (DMSO, 125 MHz) δ 156.3, 135.9, 129.1, 128.1, 122.1, 100.9, 71.5, 68.2, 45.6, 29.9; Elemental Analysis Calcd for $C_{10}H_{12}BrNO_2$—HCl: C, 40.77; H, 4.44; N, 4.75. Found: C, 40.77; H, 4.63; N, 4.63.

General Procedure for the Preparation of 2-Amino-3-(substituted-phenyl)-propanol

(S)-[2-(3-Bromo-phenyl)-1-hydroxymethyl-ethyl]-carbamic acid tert-butyl ester

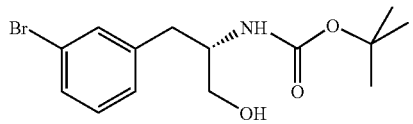

To a solution of (S)-3-(3-bromo-phenyl)-2-tert-butoxycarbonylamino-propinic acid (500 mg, 1.45 mmol) in THF (30 mL) was added borane-tetrahydrofuran complex (1.0 M solution) (4.35 mL, 4.35 mmol). The reaction mixture was stirred at room temperature for 14 h and quenched with acetic acid (1 mL). After removal of most solvent, the residue was extracted with EtOAc, washed with brine, dried over $Na_2SO_4$. After concentration, the crude product (400 mg, 83%) was used for the next step without purification. LCMS (M+H)$^+$ m/z 330 (t=1.61 min).

(S)-2-Amino-3-(3-bromo-phenyl)-propan-1-ol

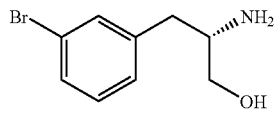

To a solution of (S)-[2-(3-bromo-phenyl)-1-hydroxymethyl-ethyl]-carbamic acid tert-butyl ester (400 mg, 1.21 mmol) in methanol (30 mL) was added 4 N HCl in dioxane (2 mL, excess). The reaction mixture was stirred at room temperature for 14 h. After concentration in vacuo, the residue was used for the next step without purification. LCMS (M+H)$^+$ m/z 230 (t=0.78 min.)

Preparation of 3-(6-Imidazol-1-yl-4-methyl-1H-benzimidazol-2-yl)-4-iodo-1H-pyridin-2-one 1-(3-Methyl-4-nitro-phenyl)-1H-imidazole

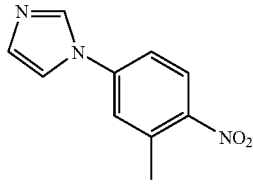

To a solution of 4-fluoro-2-methyl-1-nitro-benzene (300 mg, 1.84 mmol) in DMSO (2 mL) were added KOH (20 mg, 3.87 mmol) and imidazole (263 mg, 3.88 mmol). The reaction mixture was heated to 100° C. for 3.5 h, cooled to room temperature, and diluted with ice-cold water. The resulting precipitate was filtered, washed with ice-cold water, and dried under vacuum to give the title compound (310 mg, 80%) as a yellow powder. $^1$H NMR (300 MHz, DMSO-$d_6$) δ 8.46 (1H, s), 8.16 (1H, d, J=8.9 Hz), 7.90-7.92 (2H, m), 7.78 (1H, dd, J=2.5, 8.9 Hz), 7.17 (1H, s), 2.61 (3H, s). LRMS (M+H)$^+$ m/z 204.

4-Imidazol-1-yl-2-methyl-phenylamine

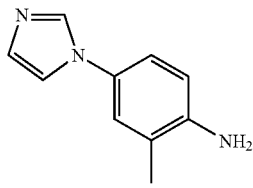

To 1-(3-methyl-4-nitro-phenyl)-1H-imidazole (200 mg, 0.98 mmol) and 10% Palladium on carbon (35 mg) was added degassed methanol (3 mL). The suspension was flushed and evacuated with hydrogen/vacuum line. The suspension was allowed to stir at room temperature for 14 h under hydrogen atmosphere (hydrogen balloon). The dark reaction mixture was filtered through a pad of celite and rinsed with methanol. Concentration of the filtrate gave the title compound (166 mg, 98%) which was used for the next step without purification. $^1$H NMR (300 MHz, DMSO-$d_6$) δ 7.95 (1H, s), 7.48 (1H, s), 7.16 (1H, narrow d, J=2.5 Hz), 7.09 (1H, dd, J=2.5, 8.4 Hz), 7.01 (1H, s), 6.67 (1H, d, J=8.4 Hz), 5.03 (2H, broad s), 2,10 (3H, s).

N-(4-Imidazol-1-yl-2-methyl-6-nitro-phenyl)-acetamide

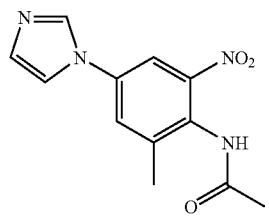

To a solution of 4-imidazol-1-yl-2-methyl-phenylamine (1 g, 5.78 mmol) in CH$_2$Cl$_2$ (20 mL) was added Ac$_2$O (0.7 mL, 7.28 mmol) at 0° C. The reaction mixture was stir at room temperature for 14 h and diluted with water. The aqueous layer was extracted with CH$_2$Cl$_2$ and the combined organic layers were washed with saturated NaHCO$_3$ and brine, dried over Na$_2$SO$_4$, and concentrated in vacuo to give a white solid. The white solid was suspended in H$_2$SO$_4$ (conc.) (15 mL). Then HNO$_3$ (conc.) (0.312 mL) was added to the suspension at 0° C. The reaction mixture was slowly warmed to room temperature and stirred at room temperature for 4 h. After cooling to −10° C., the reaction mixture was neutralized with ammonium hydroxide and extracted with ethyl acetate. The combined organic layers were washed with brine, dried over Na$_2$SO$_4$, and concentrated. The residue was purified by flash chromatography (1:9:5 MeOH/THF/hexane) to yield the title compound (0.61 g, 41%). $^1$H NMR (300 MHz, CD$_3$OD) δ 8.11 (1H, s), 7.45-7.56 (2H, m), 7.38 (1H, dd, J=2.4, 8.4 Hz), 7.14 (1H, s), 2.33 (3H, s), 2.18 (3H, s).

4-Imidazol-1-yl-2-methyl-6-nitro-phenylamine

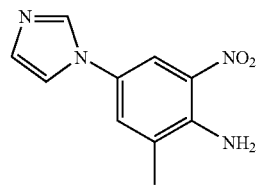

To a suspension of N-(4-imidazol-1-yl-2-methyl-6-nitro-phenyl)-acetamide (279 mg, 1.07 mmol) in ethanol (3 mL) was added 2 N HCl (2 mL). The reaction mixture was heated to reflux for 14 h, cooled to room temperature, and neutralized with saturated NaHCO$_3$. The resulting bright orange solid was filtered and dried under vacuum. The title compound (179 mg, 76%) was obtained as an orange solid. $^1$H NMR (300 MHz, CD$_3$OD) δ 8.78 (1H, s), 8.24 (1H, s), 7.78 (1H, s), 7.64 (1H, s), 7.46 (1H, s), 2.36 (3H, s).

5-Imidazol-1-yl-3-methyl-benzene-1,2-diamine

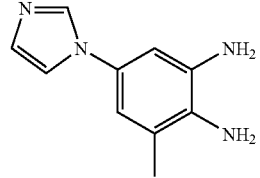

To 4-imidazol-1-yl-2-methyl-6-nitro-phenylamine (350 mg, 1.61 mmol) and 10% Palladium on carbon (40 mg) were added degassed methanol (5 mL) and TFA (5 drops). The reaction mixture was flushed and evacuated with hydrogen/vacuum line, stirred at room temperature for 14 h under hydrogen atmosphere (hydrogen balloon). The dark reaction mixture was filtered through a pad of celite and rinsed with methanol. Concentration of the filtrate gave the residue, which was diluted with water, extracted with ethyl acetate. The combined organic layers were washed with saturated NaHCO$_3$, brine, dried over Na$_2$SO$_4$. Concentration to dryness gave the title compound (275 mg, 91%) as a solid. $^1$H NMR (300 MHz, CD$_3$OD) δ 7.87 (1H, s), 7.34 (1H, s), 7.05 (1H, s), 6.72 (1H, d, J=2.4 Hz), 6.65 (1H, d, J=2.4 Hz) 2.21 (3H, s). LCMS (M+H)$^+$ m/z 189 (t=0.23 min.).

4-Amino-3-methyl-benzonitrile

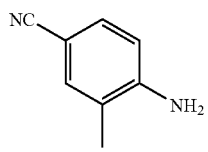

To a solution of 3-methyl-4-nitro-benzonitrile (20 g, 0.123 mol) in HOAc (200 mL) was added iron powder (17.55 g, 0.309 mol). After 10 min, the reaction was exothermic and turned to dark color. The reaction mixture was allowed to stir at room temperature for 14 h and then diluted with EtOAc (200 mL). The brown precipitate was filtered through a pad of celite and the filtercake was rinsed with EtOAc. The filtrate was concentrated in vacuo and the residue was purified by flash chromatography (40% EtOAc/hexane) to yield the title compound (15.3 g, 92%). $^1$H NMR (300 MHz, CDCl$_3$) δ 7.30-7.34 (2H, m), 6.64 (1H, d, J=8.7 Hz), 2.16 (3H, s). LCMS (M+H)$^+$ m/z 133 (t=0.93 min).

N-(4-Cyano-2-methyl-6-nitro-phenyl)-2,2,2-trifluoro-acetamide

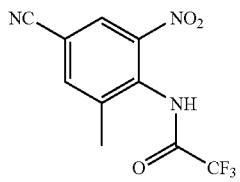

To the ice-cold trifluoroacetic anhydride (60 mL) was added 4-amino-3-methyl-benzonitrile (14.33 g, 0.108 mol) in portion. The resulting white slurry was stirred at 0° C. for 30 min. Then ammonium nitrate (17.28 g, 0.216 mol) was added. The reaction mixture was allowed to stir at 0° C. for 1 h and at room temperature for 14 h. After removal of most solvent, the reaction mixture was cooled with ice and quenched with ice. The yellow precipitate was filtered, washed with cold water, and dried under vacuum. The crude product (15.5 g, 52% yield, and ca. 80% pure) was used for the next step without purification. $^1$H NMR (300 MHz, CD$_3$OD) δ 8.05 (1H, s), 7.74 (1H, s), 2.30 (3H, s). LRMS (neg. ESI, (M−H)$^−$) m/z 272.

4-Amino-3-methyl-5-nitro-benzonitrile

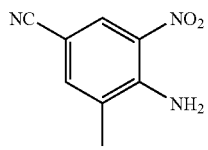

A mixture of N-(4-cyano-2-methyl-6-nitro-phenyl)-2,2,2-trifluoro-acetamide (5 g, 18.3 mmol) and 2 M ammonia in methanol (80 mL) was heated to reflux for 14 h and then cooled to room temperature. After concentration in vacuo, the residue was purified by flash chromatography (20% EtOAc/hexane) to yield the title compound (3.24 g, 100%, ca 80% pure). $^1$H NMR (300 MHz, CDCl$_3$) δ 8.40 (1H, s), 7.47 (1H, s), 6.6-6.8 (2H, broad s), 2.89 (3H, s).

3,4-Diamino-5-methyl-benzonitrile

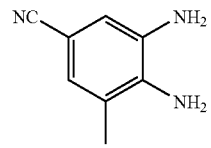

To a solution of 4-amino-3-methyl-5-nitro-benzonitrile (3.24 g, 18.3 mmol) in ethanol (80 mL) was added tin chloride dihydrate (8.67 g, 49.75 mmol). The reaction mixture was heated to reflux for 14 h, then cooled to room temperature, and concentrated in vacuum. The residue was diluted with ethyl acetate (100 mL) and treated with triethylamine (20 mL). The resulting slurry was filtered through a pad of celite and the filtercake was rinsed with three-portion ethyl acetate (50 mL). The filtrate was washed with saturated NaHCO$_3$, water, and brine, then dried over Na$_2$SO$_4$ and filtered. After removal of solvent, the residue was purified by flash chromatography on silica gel (30%-50% EtOAc/hexane) to yield the title compound (2.17 g, 81%) as a light yellow solid. $^1$H NMR (300 MHz, CDCl$_3$) δ 6.94 (1H, s), 6.85 (1H, s), 2.16 (3H, s). LCMS (M+H)$^+$ m/z 148 (t=0.67 min.).

5-Bromo-3-methyl-benzene-1,2-diamine

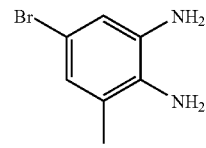

To a suspension of 4-bromo-2-methyl-6-nitro-phenylamine (20 g, 0.086 mol) in ethanol (200 mL) was added tin chloride dihydrate (49.2 g, 0.258 mol). The reaction mixture was heated to reflux for 14 h, cooled to room temperature, and concentrated in vacuo. The residue was diluted with ethyl acetate (150 mL) and treated with triethylamine (40 mL). The resulting slurry was filtered through a pad of celite, and the filtercake was rinsed with three portions ethyl acetate (50 mL). The filtrate was washed with saturated NaHCO$_3$, water, and brine, then dried over Na$_2$SO$_4$ and filtered. After removal of the solvent, the residue was purified by flash chromatography on silica gel (30% EtOAc/hexane, then 5% MeOH/CH$_2$Cl$_2$) to yield the title compound (10.26 g, 59%) as a yellow oil. $^1$H NMR (300 MHz, CDCl$_3$) δ 6.77 (1H, d, J=2.0 Hz), 6.74 (1H, d, J=2.0 Hz), 2.16 (3H, s). LCMS (M+H)$^+$ m/z 201. (t=0.83 min.).

1-[4-(4-Amino-3-methyl-5-nitro-phenyl)-piperazin-1-yl]-ethanone

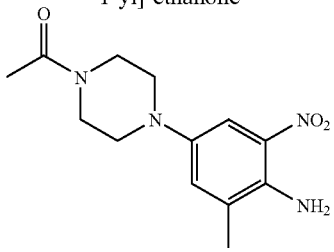

A mixture of 4-bromo-2-methyl-6-nitro-phenylamine (5 g, 21.64 mmol), 1-acetylpiperazine (4.2 g, 32.46 mmol), palladium acetate (244 mg, 1.08 mmol), tri-tert-butylphosphine (440 mg, 2.16 mmol) and sodium tert-butoxide (4.2 g, 43.29 mmol) in toluene (70 mL) was heated to 100° C. for 14 h under nitrogen. The reaction mixture was cooled to room temperature and diluted with EtOAc. After extraction, the combined organic layers were washed with water, brine, dried over $Na_2SO_4$. Concentration gave a brownish residue which was purified by flash column chromatography (10% MeOH/$CH_2Cl_2$) to yield the title compound (4.21 g, 70%). $^1$H NMR (400 MHz, $CD_3OD$) δ 7.42 (1H, d, J=2.8 Hz), 7.23 (1H, d, J=2.8 Hz), 3.71 (2H, t, J=5.1 Hz), 3.67 (2H, t, J=5.1 Hz), 3.04 (2H, t, J=5.2 Hz), 2.98 (2H, t, J=5.2 Hz), 2.24 (3H, s), 2.13 (3H, s). LCMS $(M+H)^+$ m/z 279 (t=1.46 min.).

1-[4-(3,4-Diamino-5-methyl-phenyl)-piperazin-1-yl]-ethanone

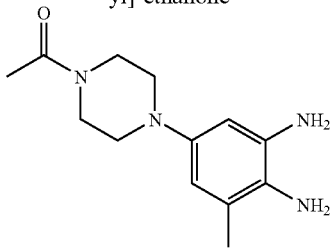

To 1-[4-(4-amino-3-methyl-5-nitro-phenyl)-piperazin-1-yl]-ethanone (4.5 g, 16.2 mmol) and 10% palladium on carbon (400 mg) were added methanol (50 mL) and acetic acid (5 mL) under nitrogen. The reaction mixture was stirred under hydrogen atmosphere (hydrogen balloon) for 14 h. The dark solution was filtered through a pad of celite and the filtercake was washed with methanol. Concentration of the filtrate gave the title compound (4.00 g, 100%) which was used for the next step without purification. LCMS $(M+H)^+$ m/z 207 (t=0.41 min.).

Procedure for the Preparation of 2-Amino-4-Fluoro-6-methyl nitrobenzene

2-(3,5-Difluoro-2-nitro-phenyl)-malonic acid di-tert-butyl ester

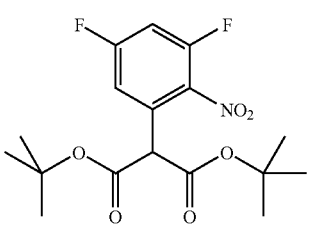

To a suspension of NaH (54.6 g, 60%, 1.365 mol) in 600 mL of DMF was added di-t-Butyl malonate (118 g, 0.546 mol) at 0° C. and stirred for 30 min. 2,4,6 trifluoronitrobenzene was added as a solution in 400 mL of DMF (75 g, 0.42 mol) over 3 hours and the solution stirred at ambient temperature for 12 hours. The reaction mixture was extracted with ethyl acetate (3×'s). The ethyl acetate was washed with water (3×'s) and with brine and dried over $MgSO_4$ and concentrated to give 62 g of crude product. LCMS [M+Na]–396; $^1$H NMR (500 MHz, DMSO) δ 7.81 (m, 1H), 7.27 (m, 1H), 5.00 (s, 1H), 1.41 (m, 18H).

2-(3-Amino-5-fluoro-2-nitro-phenyl)-malonic acid di-tert-butyl ester

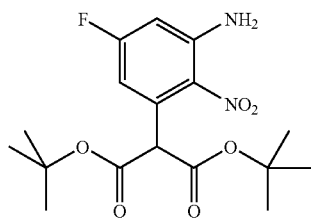

To the crude 2-(3,5-Difluoro-2-nitro-phenyl)-malonic acid di-tert-butyl ester (62 g, 0.42 mol) was added 700 mL of 2M ammonia in methanol in a pressure bottle. The vessel was sealed and heated to 85° C. for 18 hours. The reaction mixture was cooled and the vessel opened carefully and the methanol solution concentrated to provide 140 g of crude material. LCMS [M+Na]–393; $^1$H NMR (500 MHz, DMSO) δ 6.76 (dd, J=10.8 2.8 Hz, 1H), 6.29 (dd, J=10.8, 2.8 Hz, 1H), 4.99 (brs, 2H), 4.80 (s, 1H), 140 (m, 18H).

3-Amino-5-fluoro-2-nitro phenyl acetic acid

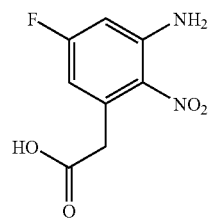

To the 2-(3-Amino-5-fluoro-2-nitro-phenyl)-malonic acid di-tert-butyl ester (140 g) in 500 mL of 4N HCl in dioxane was added 50 mL of water and heated to 40° C. for 2 days. The solution was extracted with ethyl acetate (3×'s) and the ethyl acetate washed with water (3×'s) and brine. The organic fraction was dried over $MgSO_4$ and was concentrated to give 78 g of crude (66% pure by LC/MS); $^1$H NMR (500 MHz, DMSO) δ 12.40 (brs, 1H), 7.04 (s, 2H), 6.68 (dd, J=10.9 2.8 Hz, 1H), 6.47 (dd, J=10.9, 2.8 Hz, 1H), 3.80 (s, 2H).

2-Amino-4-fluoro-6-methyl nitrobenzene

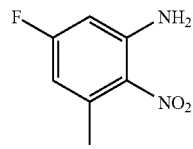

To the crude 3-Amino-5-fluoro-2-nitro phenyl acetic acid (3.6 g, 16.8 mmol) was added Cu$_2$O (10.1 g, 70.6 mmol) in 120 mL of acetonitrile along with 50 uL of methanol and the suspension was refluxed for 12 hours. The reaction mixture was filtered through Celite and the Celite pad washed with water and ethyl acetate. The filtrate was extracted with ethyl acetate, washed with water and brine, dried over Na$_2$SO$_4$ and concentrated to give 2.95 g of material which by $^1$H NMR was 80% pure. ESIMS [M+Na]–193; $^1$H NMR (500 MHz, DMSO) δ 6.67 (s, 2H), 6.56 (dd, J=11, 2.8 Hz, 1H), 6.39 (dd, J=11, 2.8 Hz, 1H), 2.50 (s, 3H).

2-Methyl-4-morpholin-4-yl-6-nitro-phenylamine

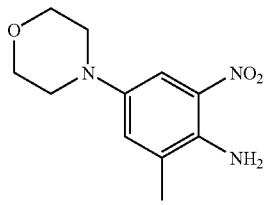

To a 800 ml pressure flask was added Tris(dibenzylideneacetone)dipalladium (2.64 g, 2.88 mmol), 2-(Di-t-butylphosphino)biphenyl (1.42 g, 4.75 mmol) and sodium tert-butoxide (17.5 g, 182 mmol). Then dry THF (500 mL), 4-bromo-2-methyl-6-nitroaniline (30.0 g, 130 mmol) and morpholine (34 ml, 390 mmol) were added. Argon was bubbled through the solution for 1 minute and the flask was sealed. The reaction mixture was stirred at 85° C. for 3 days. THF was evaporated in vacuo and the crude product was preabsorbed on silica and this then transferred on top of a silica gel column. Elution with hexane-ethyl acetate (6:4 to 4:6 to 0:1 gradient) gave, after evaporation of solvents, the title compound (15.2 g red-brown solid, 49.3%). LCMS (M+H)$^+$ m/z 238 (t=0.64 min.) $^1$H NMR (500 MHz, DMSO-d$_6$) δ 7.32 (1H, s), 7.22 (1H, s), 6.96 (2H, s), 3.72 (4H, broad s), 2.96 (4H, broad s), 2.21 (3H, s).

4-(3-Amino-5-methyl-4-nitro-phenyl)-piperazine-1-carboxylic acid tert-butyl ester

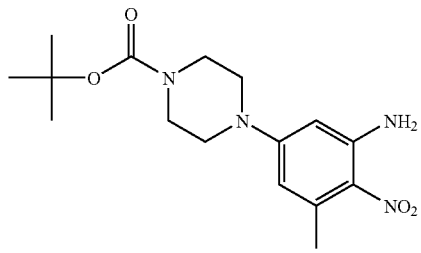

To a stirred solution of 3-fluoro-5-amino-6-nitrotoluene (10 g, 58.79 mmol) in anhydrous NMP (160 mL) under nitrogen was addded BOC-piperazine (39 g, 209.4 mmol) and 4-methylmorpholine (25.9 mL). The resulting dark solution was heated to reflux for 72 h, cooled to room temperature and diluted with ethyl acetate (4000 mL). The organic layer was washed with water (8×1500 mL), brine (1×1500 mL), dried over sodium sulfate and evaporated in vacuo. The resulting dark oil was dissolved in boiling absolute ethanol (800 mL) and concentrated to a total volume of 400 mL and left to stand overnight at room temperature. The solution was further cooled to –20° C. for 5 h and the resulting solid was filtered off and dried in vacuo to give 16.3 g (83%) of a light yellow solid. $^1$H NMR (500 MHz, CDCl$_3$) δ 6.16 (brs, 1H), 6.04 (brs, 1H), 3.70-3.60 (m,4H), 3.38-3.25 (m, 4H), 2.53 (s, 3H), 1.48 (s, 9H); LCMS (M+H)$^+$ m/z 337.

4-(3,4-Diamino-5-methyl-phenyl)-piperazine-1-carboxylic acid tert-butyl ester

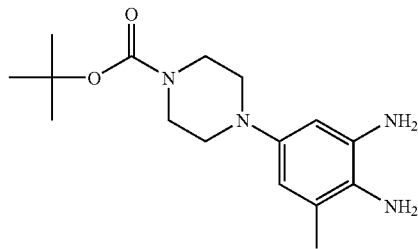

To a stirred solution of 4-(3-Amino-5-methyl-4-nitrophenyl)-piperazine-1-carboxylic acid tert-butyl ester (15 g, 44.6 mmol) in methanol (2200 mL) was added 20% Pd(OH)2/C (1.6 g) and the suspension flushed well with nitrogen, followed by hydrogen. The resulting suspension was stirred overnight at room temperature under an atmosphere of hydrogen (ca. 1 atm). The resulting suspension was filtered under nitrogen through a pad of Celite and washed with methanol (400-500 mL). The resulting material was used immediately. LCMS (M+H)$^+$ m/z 307.

[1-(3-Amino-5-methyl-4-nitro-phenyl)-piperidin-4-yl]-carbamic acid tert-butyl ester

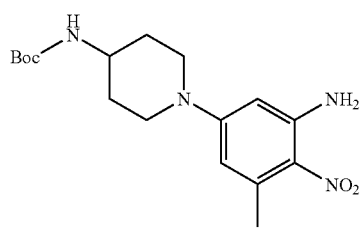

5-Fluoro-3-methyl-2-nitro-phenylamine (0.97 g, 5.7 mmol), 4-N-BOC-aminopiperidine (1.60 g, 8.0 mmol), diisopropylethylamine (2.5 ml, 14 mmol) and DMSO (10 ml) are combined and stirred at 85° C. for 3 hours. The reaction mixture was poured on saturated aqueous NaHCO$_3$ solution and extracted with ethyl acetate. The organic layers were washed with water (3×) and brine, dried over Na$_2$SO$_4$ and concentrated. Flash column chromatography on silica (eluent hexanes-ethyl acetate-triethylamine 50-50-1, then 33-66-1) gave the title compound as a yellow solid. (1.57 g, 79%). LCMS (M+H)$^+$ m/z 351 (t=1.55 min.). $^1$H NMR (500 MHz, CD$_3$OD) δ 6.70 (1H, broad s), 6.22 (1H, d, J=2.5 Hz)), 6.13 (1H, d, J=2.5 Hz), 3.88 (2H, d, J=13.3 Hz), 3.58 (1H, broad s), 2.98 (2H, t, J=11.8 Hz), 2.48 (3H, s), 1.92 (2H, J=11.3 Hz), 1.48 (2H, m), 1.45 (9H, s).

3-Methyl-5-(2-morpholin-4-ethoxy)-2-nitro-phenylamine

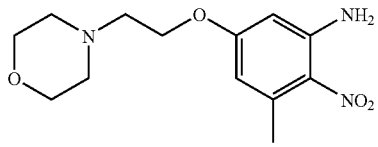

To a solution of 2-morpholin-4-yl-ethanol (5 g, excess) in THF (30 mL) was added NaH (0.21 g, 8.82 mmol) in portion under ice bath. The reaction mixture was stirred at room temperature for 30 min. Then 5-fluoro-3-methyl-2-nitrophenylamine was added. The reaction mixture was heated to reflux for 6 h, cooled to room temperature, and concentrated. The residue was diluted with water and extracted with EtOAc. The combined organic layers were washed with water, brine, and dried over Na$_2$SO$_4$. After concentration, the residue was purified by column chromatography (20% EtOAc/hexane) to yield the title compound (0.70 g, 85%). $^1$H NMR (400 MHz, CD$_3$OD) δ 6.10 (1H, s), 6.09 (1H, s), 4.38-4.42 (2H, m), 3.92-4.08 (4H, m), 3.72 (1H, d, J=12 Hz), 3.53-3.56 (2H, m), 3.05-3.10 (2H, m), 2.48 (3H, s). LCMS (M+H)$^+$ m/z 282 (t=0.73 min.).

5-(1,4,5,6-Tetrahydropyrimidin-1-yl)-3-methyl-2-nitro aniline

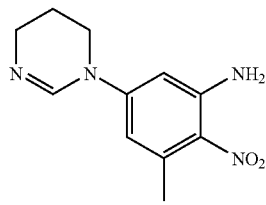

To a stirred solution of 2.0 g (11.76 mmol) of the 5-Flouro-3-methyl-2-nitro aniline in 10 mL of DMSO was added 1.2 g (14.11 mmol) of 1,4,5,6-Tetrahydropyrimidine, and 2.43 g (17.64 mmol) of potassium carbonate, and the mixture was heated at 100° C. for 10 hrs, cooled, diluted with water, and extracted with Ethylacetate containing 5% methanol. The combined organic extract was washed with water, brine and dried (Na$_2$SO$_4$). Evaporation of the solvent furnished the residue, which was chromatographed (20% of 2M ammonia in methanol and dichloromethane) to produce 1.85 g (67%) of the product as red solid. $^1$H NMR (400 MHz, CD$_3$OD) δ 7.89 (1H, s), 6.53 (1H, d, J=2.57 Hz), 6.44 ((1H, d, J=2.1 Hz), 7.04 (1H, d, J=2.1 Hz), 3.70 (2H, t, J=6.0 Hz), 3.41 (2H, t, J=5.65 Hz), 2.43 (3H, s), 2.05 (2H, m) LCMS (M+H)$^+$ m/z 235 (t=0.78 min).

2,4-Dichloro-quinoline-3-carboxaldehyde

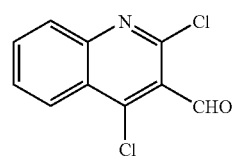

A stirred solution of 5.0 gm (25.3 mmol) of the 2,4-Dihcloro quinoline was cooled to −78° C., to which was added dropwise a 14 mL (27.8 mml) of 2M solution of lithium diisopropylamide in tetrahydrofuran under nitrogen atmosphere, stirred for 30 min, and then was added 4.9 mL (65.3 mmol) of dimethylformamide. The reaction mixture was stirred at −78° C. for 3 hrs, allowed to warm to room temperature, quenched with saturated NH$_4$Cl solution, diluted with water, and extracted with ethyl acetate. The combined organic extract was washed with water, brine, and dried (Na$_2$SO$_4$), and the solvent was evaporated to furnish the residue which was chromatographed (10% ethylacetae/hexanes) to afford the pure product. LRMS [M+H]+226; $^1$H NMR (400 MHz, CDCl$_3$) δ 10.63 (s, 1H), 8.39 (d, 1H, J=8.8 Hz), 8.06 (d, 1H, J=8.4 Hz), 7.92 (dd, 1H, J=8.4, 8.8 Hz), 7.75 (dd, 1H, J=8.8, 8.4 Hz).

1-{4-[2-(2,4-Dichloro-quinoline-3yl)-7-methyl-3H-benzimidazole-5-yl]-piperazin-1-yl}-ethanone (Scheme III)

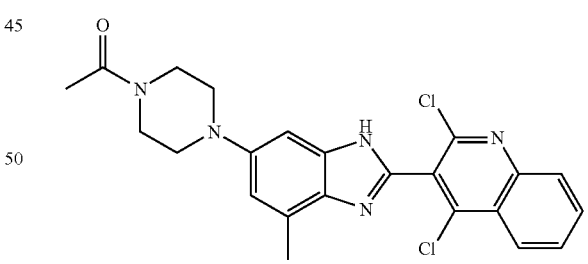

A 3.6 mmol of 1-[4-(3,4-Diamino-5-methyl-phenyl)-piperazin-1-yl]-ethanone was taken in 40 mL of methanol, to which was added 0.921 gm (3.6 mmol) of the 2,4-Dichloro-quinoline-3-carboxaldehyde, and the mixture was stirred for 10 hrs at room temperature, solvent was evaporated to dryness, and the residue was chromatographed to provide the product. LRMS [M+H]+454; $^1$H NMR (400 MHz, CDCl$_3$) δ 8.12 (d, 1H, J=7.6 Hz), 8.04 (d, 1H, J=8.4 Hz), 7.85 (dd, 1H, J=7.6, 8.4 Hz), 7.78 (dd, 1H, J=7.6, 8.4 Hz), 6.86 (brs, 1H), 6.83(brs, 1H), 3.76 (br, 2H), 3.62 (br, 2H), 3.15 (br, 2H), 3.01 (br, 2H), 2.66 (s, 3H), 2.22 (s, 3H).

3-[6-(4-Acetyl-piperazin-1-yl)-4-methyl-1H-benzoimidazol-2-yl]-4-chloro-1H-quinoline-2-one and
3-[6-(4-Acetyl-piperazin-1-yl)-4-methyl-1H-benzoimidazol-2-yl]-2-chloro-1H-quinoline-4-one
(Scheme III)

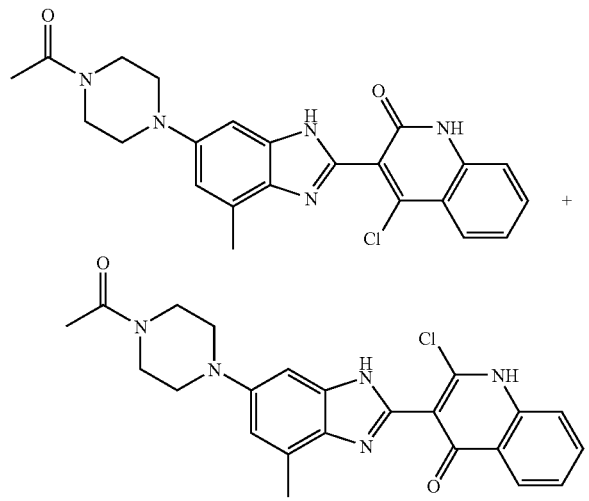

A 1.1 gm (2.42 mmol) of the 1-{4-[2-(2,4-Dichloro-quinoline-3yl)-7-methyl-3H-benzimidazole-5-yl]-piperazin-1-yl}-ethanone was taken in 10 mL of 4N hydrochloric acid in dioxane, to which was added 2 mL of water, and the mixture was heated at 50° C. for 12 hrs, solvent was evaporated to dryness, and the residue was subjected to preparative HPLC to afford the products.

3-[6-(4-Acetyl-piperazin-1-yl)-4-methyl-1H-benzoimidazol-2-yl]-4-chloro-1H-quinoline-2-one: LRMS [M+H]+ 436; $^1$H NMR (400 MHz, CDCl$_3$) δ 8.19 (d, 1H, J=7.6 Hz), 7.82 (dd, 1H, J=7.6, 8.4 Hz), 7.49 (m, 2H), 7.28 (brs, 1H), 7.06 (brs, 1H), 3.77 (m, 4H), 3.30 (m, 4H), 2.65 (s, 3H), 2.15 (s, 3H).

3-[6-(4-Acetyl-piperazin-1-yl)-4-methyl-1H-benzoimidazol-2-yl]-2-chloro-1H-quinoline-4-one: LRMS [M+H]+ 436; $^1$H NMR (400 MHz, CDCl$_3$) δ 8.32 (d, 1H, J=8.2 Hz), 7.86 (dd, 1H, J=8.2, 8.4 Hz), 7.67 (d, 1H, J=8.4 Hz), 7.58 (dd, 1H, J=8.2, 8.4 Hz), 7.25 (brs, 1H), 7.06 (brs, 1H), 3.77 (m, 4H), 3.33 (m, 4H), 2.63(s, 3H), 2.17 (s, 3H).

4-Chloro-3-(4-methyl-6-piperazin-1-yl-1H-benzimidazole-2yl)-1H-quinolin-2-one and 2-Chloro-3-(4-methyl-6-piperazin-1-yl-1H-benzimidazole-2yl)-1H-quinolin-4-one (Scheme III)

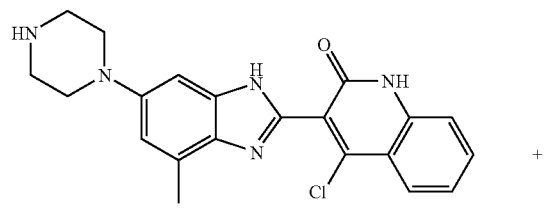

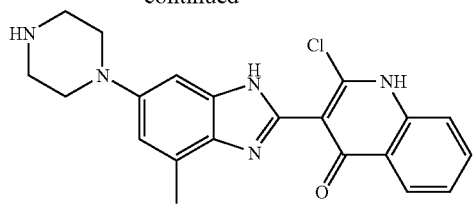

A 0.45 gm (1.0 mmol) of the 1-{4-[2-(2,4-Dichloro-quinoline-3yl)-7-methyl-3H-benzimidazole-5-yl]-piperazin-1-yl}-ethanone and was taken in 5 mL of 4N hydrochloric acid in dioxane, to which was added 0.5 mL of water, and the mixture was heated at 80° C. for 10 hrs, solvent was evaporated to dryness, and the residue was used in the next step without any further purification. For product 4-Chloro-3-(4-methyl-6-piperazin-1-yl-1H-benzimidazole-2yl)-1H-quinolin-2-one: LRMS [M+H]+ 394; 2-Chloro-3-(4-methyl-6-piperazin-1-yl-1H-benzimidazole-2yl)-1H-quinolin-4-one: LRMS [M+H]+ 394.

EXAMPLES 1 AND 2 (SCHEME III)

Example 1

3-[6-(4-Acetyl-piperazin-1-yl)-4-methyl-1H-benzoimidazol-2-yl]-4-[(S)-2-(3-chloro-pheny)-2-hydroxy-ethylamino]-1H-quinoline-2-one and Example 2

3-[6-(4-Acetyl-piperazin-1-yl)-4-methyl-1H-benzoimidazol-2-yl]-2-[(S)-2-(3-chloro-phenyl)-2-hydroxy-ethlamino]-1H-quinoline-4-one

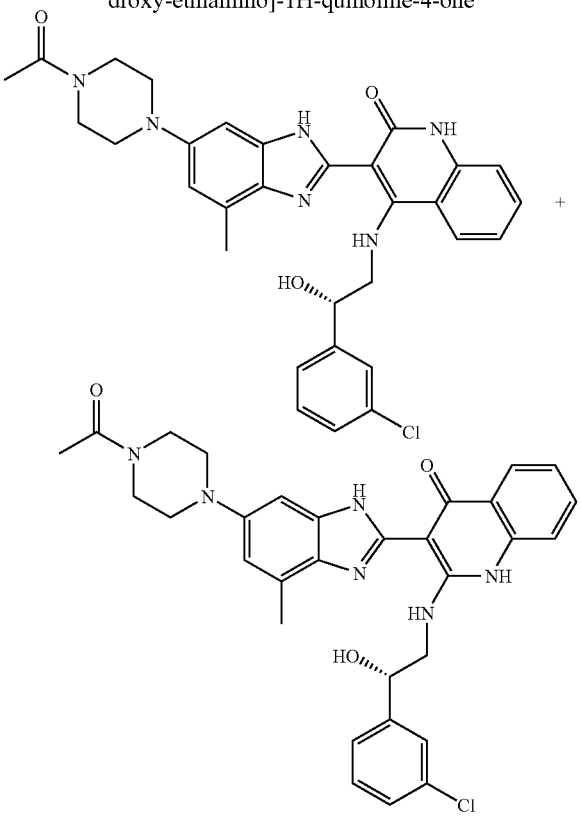

A stirred solution of 100 mg of (0.23 mmol) of the mixture of 3-[6-(4-Acetyl-piperazin-1-yl)-4-methyl-1H-benzoimidazol-2-yl]-4-chloro-1H-quinoline-2-one and 3-[6-(4-Acetyl-piperazin-1-yl)-4-methyl-1H-benzoimidazol-2-yl]-2-chloro-1H-quinoline-4-one were taken in 3 mL of dimethylformamide and 0.5 mL of N-methyl morpholine and a 0.988 gm (057 mmol) of the (S)-2-(3-Chloro-phenyl)-2-hydroxy-ethylamine, and the mixture was stirred at 80° C. for 14 h, cooled and subjected to preparative HPLC to afford the products. Example 1: 3-[6-(4-Acetyl-piperazin-1-yl)-4-methyl-1H-benzoimidazol-2-yl]-4-[(S)-2-(3-chloro-phenyl)-2-hydroxy-ethylamino]-1H-quinoline-2-one: LRMS [M+H]+571; ¹H NMR (400 MHz, CDCl₃) δ 8.19 (d, 1H, J=7.8 Hz), 7.97 (s, 1H), 7.25-7.62 (m, 7H), 7.13 (brs, 1H), 507 (m, 1H), 3.75-397(m, 6H), 3.31-3.47 (m, 4H), 2.60 (s, 3H), 2.15 (s, 3H). Example 2: 3-[6-(4-Acetyl-piperazin-1yl)-4-methyl-1H-benzoimidazol-2-yl]-2-[(S)-2-(3-chloro-phenyl)-2-hydroxy-ethylamino]-1H-quinoline-4one: LRMS [M+H]+571; ¹H NMR (400 MHz, CDCl₃) δ 8.19 (d, 1H, J=7.9 Hz), 7.79 (s, 1H), 7.26-7.62 (m, 7H), 7.18 (brs, 1H), 5.06 (m, 1H), 3.78(m, 6H), 3.49 (m, 4H), 2.62 (s, 3H), 2.17 (s, 3H).

Example 3

4-[(S)-2-(3-chloro-phenyl)-2-hydroxy-ethylamino]-3-(4-methyl-6-peperazin-1-yl-1H-benzimidazole-2-yl)-1H-quinoline-2-one and Example 4

2-[(S)-2-(3-chloro-phenyl)-2-hydroxy-ethylamino]-3-(4-methyl-6-piperazin-1-yl-1H-benzimidazole-2-yl)-1H-quinoline-4-one

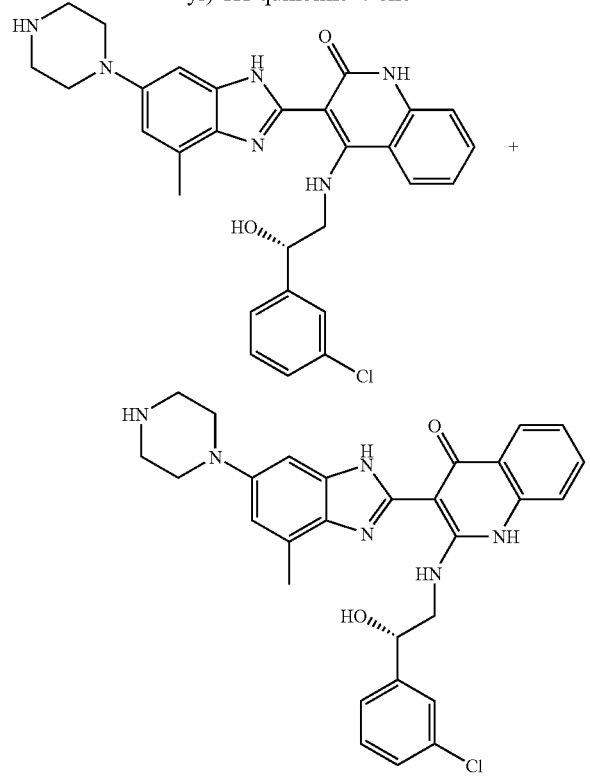

A 100 g (0.25 mmol) of (mixture of 4-Chloro-3-(4-methyl-6-piperazin-1-yl-1H-benzimidazole-2yl)-1H-quinolin-2-one and 2-Chloro-3-(4-methyl-6-piperazin-1-yl-1H-benzimidazole-2yl)-1H-quinolin-4-one were taken in 2 mL of N-methylpyrrolidine and 0.5 mL of N-methyl morpholine, to which was added 0.089 gm (0.51 mml) of (S)-2-(3-Chloro-phenyl)-2-hydroxy-ethylamine, and the mixture was heated at 80° C. for 12 hrs, cooled, and subjected to preparative HPLC to afford the products. Example 3: 4-[(S)-2-(3-chloro-phenyl)-2-hydroxy-ethylamino]-3-(4-methyl-6-piperazin-1-1H-benzimidazole-2-yl)-1H-quinoline-2-one: LRMS [M+H]+529; ¹H NMR (400 MHz, CDCl₃) δ 8.06 (d, 1H, J=8.1 Hz), 7.97 (s, 1H), 7.64 (dd, 1H, J=8.1, 7.4 Hz), 7.02-7.36 (m, 7H), 4.79 (m, 1H), 3.42-3.52(m, 8H), 3.31-3.37 (m, 4H), 2.91 (m, 2H), 2.61 (s, 3H). Example 4: 2-[(S)-2-(3-chloro-phenyl)-2-hydroxy-ethylamino]-3-(4-methyl-6-piperazin-1-yl-1H-benzimidazole-2-yl)-1H-quinoline-4one: LRMS [M+H]+529; ¹H NMR (400 MHz, CDCl₃) δ 8,22 (d, 1H, J=8.0 Hz), 7.06-7.66 (m, 9H), 5.05 (m, 1H), 3.82(m, 2H), 3.45 (m, 8H), 2.63 (s, 3H).

Example 5

4-[(S)-2-(3-chloro-phenyl)-2-hydroxy-ethylamino]-3-{6-[4-(2-hydroxy-ethyl)-piperazin-1-yl]-4methyl-1H-benzimidazole-2-yl}-1H-quinoline-2-one

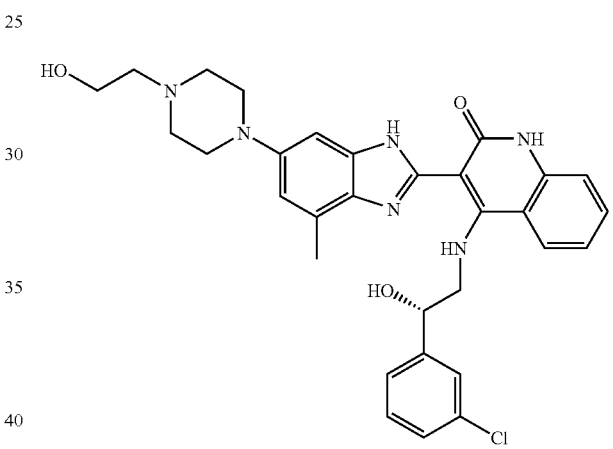

To a stirred solutionof 12 mg (0.023 mmol) of the 4-[(S)-2-(3-chloro-phenyl)-2-hydroxy-ethylamino]-3-(4-methyl-6-piperazin-1-yl-1H-benzimidazole-2-yl)-1H-quinoline-2-one in 0.5 mL of methanol was added ~5 mg of glycaldehyde to which was added 0.3 mL of 1 N solution of sodiumcyanoborohydride in tetrahydrofuran, and the mixture was stirred for 30 minutes, and then it was subjected to preparative HPLC to afford the product. LRMS [M+H]+ 573; ¹H NMR (400 MHz, CDCl₃) δ 8.06 (d, 1H, J=7.96 Hz), 7.97 (s, 1H), 7.64 (dd, 1H, J=7.97, 8.4 Hz), 7.03-7.36 (m, 7H), 4.77 (m, 1H), 3.94 (t, 1H, J=5.1 Hz), 3.42-3.52(m, 8H), 3.36 (t, 1H, J=5.1 Hz), 3.31-3.47 (m, 4H), 2.63 (s, 3H).

It is understood that the examples described above in no way serve to limit the true scope of this invention, but rather are presented for illustrative purposes. All references cited herein are incorporated by reference in their entirety.

What is claimed is:
1. A compound selected from the group consisting of
3-[6-(4-Acetyl-piperazin-1-yl)-4-methyl-1H-benzoimidazol-2-yl]-4-[(S)-2-(3-chloro-phenyl)-2-hydroxy-ethlamino]-1H-quinoline-2-one;
3-[6-(4-Acetyl-piperazin-1-yl)-4-methyl-1H-benzoimidazol-2-yl]-2-[(S)-2-(3-chloro-phenyl)-2-hydroxy-ethlamino]-1H-quinoline-4-one;

4-[(S)-2-(3-chloro-phenyl)-2-hydroxy-ethylamino]-3-(4-methyl-6-piperazin-1-yl-1H-benzimidazole-2-yl)-1H-quinoline-2-one;

2-[(S)-2-(3-chloro-phenyl)-2-hydroxy-ethylamino]-3-(4-methyl-6-piperazin-1-yl-1H-benzimidazole-2-yl)-1H-quinoline-4-one; and 4-[(S)-2-(3-chloro-phenyl)-2-hydroxy-ethylamino]-3-{6-[4-(2-hydroxy-ethyl)-piperazin-1-yl]4-methyl-1H-benzimidazole-2-yl}-1H-quinoline-2-one.

2. A pharmaceutical composition comprising a compound according to claim 1 and a pharmaceutically acceptable carrier.

* * * * *